United States Patent
Madsen et al.

(10) Patent No.: US 8,987,197 B2
(45) Date of Patent: Mar. 24, 2015

(54) PROTEASE STABILIZED, PEGYLATED INSULIN ANALOGUES AND USES THEREOF

(75) Inventors: Peter Madsen, Bagsværd (DK); Thomas Hoeg-Jensen, Klampenborg (DK); Thomas Børglum Kjeldsen, Virum (DK); Tina Møller Tagmose, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/306,411

(22) Filed: Nov. 29, 2011

(65) Prior Publication Data

US 2012/0071402 A1    Mar. 22, 2012

Related U.S. Application Data

(63) Continuation of application No. 12/669,189, filed as application No. PCT/EP2008/058881 on Jul. 9, 2008, now abandoned.

(60) Provisional application No. 61/011,977, filed on Jan. 23, 2008, provisional application No. 60/959,863, filed on Jul. 17, 2007.

(30) Foreign Application Priority Data

| Jul. 16, 2007 | (EP) | ..................................... 07112505 |
| Sep. 20, 2007 | (WO) | ................. PCT/EP2007/059990 |
| Jan. 23, 2008 | (EP) | ..................................... 08100819 |

(51) Int. Cl.
  *A61K 38/28* (2006.01)
  *A61P 3/10* (2006.01)
  *C07K 14/62* (2006.01)
  *A61K 47/48* (2006.01)

(52) U.S. Cl.
  CPC .......... *A61K 38/28* (2013.01); *A61K 47/48215* (2013.01); *C07K 14/62* (2013.01)
  USPC ............... 514/5.9; 514/6.1; 514/6.2; 514/6.3; 514/6.8; 514/6.9; 530/303

(58) Field of Classification Search
  None
  See application file for complete search history.

(56) References Cited

U.S. PATENT DOCUMENTS

| 6,770,625 | B2 | 8/2004 | Soltero et al. | |
| 6,867,183 | B2 | 3/2005 | Soltero et al. | |
| 7,030,082 | B2 | 4/2006 | Soltero et al. | |
| 2002/0198140 | A1* | 12/2002 | Havelund .......................... 514/3 |
| 2003/0083232 | A1 | 5/2003 | Soltero et al. | |
| 2006/0019874 | A1 | 1/2006 | Radhakrishnan et al. | |
| 2008/0171695 | A1* | 7/2008 | Garibay et al. .................... 514/3 |

FOREIGN PATENT DOCUMENTS

| WO | WO 90/01038 | 2/1990 |
| WO | WO 02/098446 | 12/2002 |
| WO | WO 2006/079641 | 8/2006 |

OTHER PUBLICATIONS

Hinds et al., Adv. Drug Del. Reviews 54: 505-530, 2002.*
Chu et al., "The A14 Position of Insulin Tolerates Considerable Structural Alterations with Modest Effects on the Biological Behavior of the Hormone", Journal of Protein Chemistry, 1992, vol. 11, No. 5, pp. 571-577.
Hinds, K.D. et al., "Effects of PEG Conjugation on Insulin Properties", Advanced Drug Delivery Reviews, 2002, vol. 54, pp. 505-530.

* cited by examiner

*Primary Examiner* — Gyan Chandra
(74) *Attorney, Agent, or Firm* — Rosemarie R. Wilk-Orescan

(57) ABSTRACT

Novel PEGylated insulin analogs exhibiting resistance towards proteases can, effectively, be administered pulmonary or orally. The insulin analogs contain B25H and A14E or A14H. The PEGylation is at B29K.

10 Claims, 2 Drawing Sheets

US 8,987,197 B2

PROTEASE STABILIZED, PEGYLATED INSULIN ANALOGUES AND USES THEREOF

CROSS-REFERENCE TO RELATED APPLICATIONS

This application is a continuation of U.S. application Ser. No. 12/669,189, national stage commencement Mar. 18, 2010, which was a 35 U.S.C. §371 national stage application of International Patent Application PCT/EP2008/058881 (published as WO 2009/010428 A1), filed Jul. 9, 2008, which claimed priority of European Patent Application 07112505.8, filed Jul. 16, 2007, European Patent Application PCT/EP2007/059990, filed Sep. 20, 2007, and European Patent Application 08100819.5, filed Jan. 23, 2008; and further claimed priority under 35 U.S.C. §119 of U.S. Provisional Application 60/959,863, filed Jul. 17, 2007 and U.S. Provisional Application 61/011,977, filed Jan. 23, 2008.

FIELD OF THIS INVENTION

The present invention relates to novel PEGylated insulin analogues exhibiting resistance towards proteases, a method for the preparation of such insulin analogues, insulin preparations containing the insulin analogues of the invention and a method of treating diabetes mellitus using these insulin analogues.

BACKGROUND OF THIS INVENTION

Diabetes mellitus is a metabolic disorder in which the ability to utilize glucose is partly or completely lost. About 5% of all people suffer from diabetes and the disorder approaches epidemic proportions. Since the introduction of insulin in the 1920's, continuous efforts have been made to improve the treatment of diabetes mellitus. Since people suffering from diabetes are subject to chronic treatment over several decades, there is a major need for safe, convenient and life quality improving insulin formulations.

Human insulin consists of two polypeptide chains, the so-called A and B chains which contain 21 and 30 amino acid residues, respectively, and which are interconnected by two cystine disulphide bridges.

The oral route is by far the most widely used route for drug administration and is in general very well accepted by patients, especially for chronic therapies. Administration of therapeutic peptides or proteins is however often limited to parenteral routes rather than the preferred oral administration due to several barriers such as enzymatic degradation in the gastrointestinal (GI) tract and intestinal mucosa, drug efflux pumps, insufficient and variable absorption from the intestinal mucosa, as well as first pass metabolism in the liver.

Normally, insulin formulations are administered by subcutaneous injection. However, administration by other routes, e.g., orally or pulmonary, would be advantageous due to patient compliance, safety and convenience. Some of the commercial available insulin formulations are characterized by a fast onset of action and other formulations have a relatively slow onset but show a more or less prolonged action.

Recent formulation designs for oral protein/peptide delivery include co-formulations with protease inhibitors, permeation enhancers, polymer-based delivery systems and insulin conjugates. The latter includes hexyl-insulin-monoconjugate-2 (HIM2), a human insulin analogue with a PEG 7-hexyl group attached to B29. In for example U.S. Pat. No. 7,030,082; U.S. Pat. No. 6,867,183 and U.S. Pat. No. 6,770,625, oral HIM2 has been reported to have increased proteolytic stability and bioavailability compared to insulin. For example, WO 02/098446 relates to a substantially monodisperse mixture of conjugates, each conjugate comprising a drug coupled to an oligomer that comprises a polyalkylene glycol moiety wherein said drug is a polypeptide, for example, an insulin peptide. In example 124 of WO 02/098446, some insulin-oligomer conjugates are described wherein the insulin peptide is human insulin; human insulin is not stable against enzymes, i.e., not stable against chymotrypsin. According to claim 1, US 2006/0019874 A1 relates to a complex comprising (a) an insulin compound conjugate comprising an insulin compound conjugated to a modifying moiety, and (b) a cation, wherein the insulin compound conjugate is complexed with the cation.

ASPECTS OF THIS INVENTION

An aspect of this invention relates to the furnishing of insulin analogues which, when administered orally, can give a satisfactory control of the blood glucose level.

Another aspect of this invention relates to the furnishing of insulin analogues which, when administered pulmonarily, can give a satisfactory control of the blood glucose level.

Another aspect of this invention relates to the furnishing of insulin analogues which, when administered pulmonarily, can give a satisfactory control of the blood glucose level with a relatively slow onset and a more or less prolonged action.

The object of this invention is to overcome or ameliorate at least one of the disadvantages of the prior art, or to provide a useful alternative.

DEFINITIONS

Herein, the term insulin covers natural occurring insulins, e.g., human insulin, as well as insulin analogues thereof.

Herein the term amino acid residue covers an amino acid from which a hydrogen atom has been removed from an amino group and/or a hydroxy group has been removed from a carboxy group and/or a hydrogen atom has been removed from a mercapto group. Imprecise, an amino acid residue may be designated an amino acid.

Herein, hydrophobic amino acids are to be understood as the naturally occurring amino acids tryptophan (Trp, W), phenylalanine (Phe, F), valine (Val, V), isoleucine (Ile, I), leucine (Leu, L) and tyrosine (Tyr, Y) (with the three-letter and the one-letter abbreviation in brackets).

Herein, hydrophilic amino acids are to be understood as natural amino acids that are not hydrophobic amino acids according to the definition above. In one embodiment hydrophilic acids according to the invention are selected from the group consisting of: Glutamic acid (Glu, E), aspartic acid (Asp, D), histidine (His, H), glutamine (Gln, Q), asparagine (Asn, N), serine (Ser, S), threonine (Thr, T), proline (Pro, P), glycine (Gly, G), lysine (Lys, K) and arginine (Arg, R). In a further embodiment hydrophilic amino acids according to the invention are selected from the group consisting of: Glutamic acid (Glu, E), aspartic acid (Asp, D), histidine (His, H), glutamine (Gln, Q), asparagine (Asn, N), lysine (Lys, K) and arginine (Arg, R).

Herein, the term insulin analogue covers a polypeptide which has a molecular structure which formally can be derived from the structure of a naturally occurring insulin, e.g., human insulin, by deleting and/or substituting (replacing) one or more amino acid residue occurring in the natural insulin and/or by adding one or more amino acid residue. The added and/or substituted amino acid residues can either be codable amino acid residues or other naturally occurring amino acid residues or purely synthetic amino acid residues.

Herein the term daughter insulin means the insulin without an appended PEG moiety. Said daughter insulins have an improved stability against degradation from proteases.

Herein the term parent insulin means the insulin without an appended PEG moiety and without mutations to improve stability against degradation from proteases. Said parent insulins have optionally mutations relative to human insulin. Parent insulins are thus also insulin analogues as defined above.

Herein, the term mutation covers any change in amino acid sequence (substitutions and insertions with codable amino acids as well as deletions).

Herein, the term analogues of the A chain and analogues of the B chains of human insulin covers A and B chains of human insulin, respectively, having one or more substitutions, deletions and or extensions (additions) of the A and B amino acid chains, respectively, relative to the A and B chains, respectively, of human insulin.

Herein terms like A1, A2, A3 etc. indicate the position 1, 2 and 3, respectively, in the A chain of insulin (counted from the N-terminal end). Similarly, terms like B1, B2, B3 etc. indicates the position 1, 2 and 3, respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are AlaA21, GlyA21 and GlnA21, respectively.

Herein the terms A(0) or B(0) indicate the positions N-terminally neighbouring the A1 or B1 positions, respectively, in the A or B chains, respectively. The terms A(−1) or B(−1) indicate the positions of the first amino acids N-terminally to A(0) or B(0), respectively. Thus A(−2) and B(−2) indicate positions N-terminally to A(−1) and B(−1), respectively, A(−3) and B(−3) indicate positions N-terminally to A(−2) and B(−2), respectively, and so forth.

Herein terms like desB29 and desB30 indicate an insulin analogue lacking the B29 or B30 amino acid residue, respectively.

With fast acting insulin is meant an insulin having a faster onset of action than normal or regular human insulin.

With long acting insulin is meant an insulin having a longer duration of action than normal or regular human insulin.

The numbering of the positions in insulin analogues, insulins and A and B chains is done so that the parent compound is human insulin with the numbering used for it.

The term basal insulin as used herein means an insulin peptide which has a time-action of more than 8 hours, in particularly of at least 9 hours. Preferably, the basal insulin has a time-action of at least 10 hours. The basal insulin may thus have a time-action in the range from about 8 to 24 hours, preferably in the range from about 9 to about 15 hours.

Herein the term linker covers a chemical moiety which connects an —HN— group of the insulin with the —O— group of the PEG moiety. The linker does not have any influence on the desired action of the final PEGylated insulin, especially it does not have any adverse influence.

With "PEG" or polyethylene glycol, as used herein is meant any water soluble poly(ethylene oxide). The expression PEG will comprise the structure —$(CH_2CH_2O)_n$— where n is an integer from 2 to about 1000. A commonly used PEG is end-capped PEG, wherein one end of the PEG termini is end-capped with a relatively inactive group such as alkoxy, while the other end is a hydroxyl group that may be further modified by linker moieties. An often used capping group is methoxy and the corresponding end-capped PEG is often denoted mPEG. Hence, mPEG is $CH_3O(CH_2CH_2O)_n$—, where n is an integer from 2 to about 1000 sufficient to give the average molecular weight indicated for the whole PEG moiety, e.g., for mPEG Mw 2,000, n is approximately 44 (a number that is subject for batch-to-batch variation). The notion PEG is often used instead of mPEG.

Specific PEG forms of this invention are branched, linear, forked, dumbbell PEGs, and the like and the PEG groups are typically polydisperse, possessing a low polydispersity index of less than about 1.05. The PEG moieties present in an insulin will for a given molecular weight typically consist of a range of ethyleneglycol (or ethyleneoxide) monomers. For example, a PEG moiety of molecular weight 2000 will typically consist of 44±10 monomers, the average being around 44 monomers. The molecular weight (and number of monomers) will typically be subject to some batch-to-batch variation.

Other specific PEG forms are monodisperse that can be branched, linear, forked, or dumbbell shaped as well. Being monodisperse means that the length (or molecular weight) of the PEG polymer is specifically defined and is not a mixture of various lengths (or molecular weights). Herein the notion mdPEG is used to indicate that the mPEG moiety is monodisperse, using "d" for "discrete". The number in subscript after mdPEG, for example $mdPEG_{12}$, indicates the number of ethyleneglycol monomers within the monodisperse polymer (oligomer), in this case 12.

The term PEGylated insulin covers modification of insulin by attachment of one or more PEG moieties via a linker to the daughter insulin. The PEG moiety can either be attached by nucleophilic substitution (acylation) on N-terminal alpha-amino groups or on lysine residue(s) on the gamma-positions, e.g., with OSu-activated esters, or PEG moieties can be attached by reductive alkylation—also on amino groups present in the insulin molecule—using PEG-aldehyde reagents and a reducing agent, such as sodium cyanoborohydride, or, alternatively, PEG moieties can be attached to the sidechain of an unpaired cysteine residue in a Michael addition reaction using, e.g., PEG maleimide reagents.

By PEGylated insulin having insulin activity is meant a PEGylated insulin with either the ability to lower the blood glucose in mammalians as measured in a suitable animal model, which may, e.g., be a rat, rabbit, or pig model, after suitable administration, e.g., by intravenous or subcutaneous administration, or an insulin receptor binding affinity.

Herein the term alkyl covers a saturated, branched or straight hydrocarbon group having from 1 to 12 carbon atoms, preferably from 1 to 6 carbon atoms, more preferred from 1 to 4 carbon atoms.

Herein the term alkoxy covers the radical "alkyl-O—" wherein alkyl is as defined above. Representative examples are methoxy, ethoxy, propoxy (e.g., 1-propoxy and 2-propoxy), butoxy (e.g., 1-butoxy, 2-butoxy and 2-methyl-2-propoxy), pentoxy (1-pentoxy and 2-pentoxy), hexoxy (1-hexoxy and 3-hexoxy), and the like.

Herein the term alkylene covers a saturated, branched or straight bivalent hydrocarbon group having from 1 to 12 carbon atoms, preferably from 1 to 6 carbon atoms, more preferred from 1 to 4 carbon atoms. Representative examples include, but are not limited to, methylene, 1,2-ethylene, 1,3-propylene, 1,2-propylene, 1,3-butylene, 1,4-butylene, 1,4-pentylene, 1,5-pentylene, 1,5-hexylene, 1,6-hexylene, and the like.

By high physical stability is meant a tendency to fibrillation being less than 50% of that of human insulin. Fibrillation may be described by the lag time before fibril formation is initiated at a given conditions.

A polypeptide with insulin receptor and IGF-1 receptor affinity is a polypeptide which is capable of interacting with an insulin receptor and a human IGF-1 receptor in a suitable binding assay. Such receptor assays are well-know within the field and are further described in the examples. The present PEGylated insulin will not bind to the IGF-1 receptor or will have a rather low affinity to said receptor. More precisely, the PEGylated insulins of this invention will have an affinity towards the IGF-1 receptor of substantially the same magnitude or less as that of human insulin The terms treatment and treating as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The term treatment of a disease as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term prevention of a disease as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term effective amount as used herein means a dosage which is sufficient in order for the treatment of the patient to be effective compared with no treatment.

POT is the *Schizosaccharomyces pombe* triose phosphate isomerase gene, and TPI1 is the *S. cerevisiae* triose phosphate isomerase gene.

By a leader is meant an amino acid sequence consisting of a pre-peptide (the signal peptide) and a pro-peptide.

The term signal peptide is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of this invention including yeast aspartic protease 3 (YAP3) signal peptide or any functional analog (Egel-Mitani et al. (1990) YEAST 6:127-137 and U.S. Pat. No. 5,726,038) and the α-factor signal of the MFα1 gene (Thorner (1981) in The Molecular Biology of the Yeast *Saccharomyces cerevisiae*, Strathern et al., eds., pp 143-180, Cold Spring Harbor Laboratory, NY and U.S. Pat. No. 4,870,00.

The term pro-peptide means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analogue thereof.

Unless indicated explicitly, the amino acids mentioned herein are L-amino acids. Further, the left and right ends of an amino acid sequence of a peptide are, respectively, the N- and C-termini, unless otherwise specified.

The following abbreviations have been used in the specification and examples: Da is Dalton (molecular weight), kDa is kilo-Dalton (=1000 Da), mPEG-SBA is mPEG-$CH_2CH_2CH_2$—CO—OSu (N-hydroxysuccinimidyl ester of mPEG-butanoic acid), mPEG-SMB is mPEG-$CH_2CH_2CH(CH_3)$—CO—OSu (N-hydroxysuccinimidyl ester of mPEG-α-methylbutanoic acid), mPEG-SPA is mPEG-$CH_2CH_2$—CO—OSu (N-hydroxysuccinimidyl ester of mPEG-propionic acid), Mw is molecular weight, OSu is 1-succinimidyloxy=2,5-dioxopyrrolidin-1-yloxy, R is room temperature, SA is sinapinic acid and Su is 1-succinimidyl=2,5-dioxopyrrolidin-1-yl.

SUMMARY OF THE INVENTION

It has been discovered that insulins that are stabilised towards proteolytic degradation (by specific mutations) and PEGylated at the B29-lysine are efficacious and protracted and possess high potential as protracted insulins that can be administered pulmonary or orally. Furthermore, after oral administration, these PEGylated insulins of this invention have a higher degree of bioavailability than similar known PEGylated insulins, that are not stabilised towards proteolytic degradation and wherein the insulin backbone is not stabilised towards proteolytic degradation. Hence, these PEGylated insulin analogues of this invention are valuable for oral administration. Similarly, after pulmonary administration, these PEGylated protease stabilised insulins of this invention displays higher apparent potency and/or bioavailability than similar known PEGylated insulins, that are not stabilised towards proteolytic degradation and wherein the insulin backbone is not stabilised towards proteolytic degradation. Furthermore, these PEGylated protease stabilised insulins of this invention displays protracted time-action profiles when administered pulmonary to mammals. Hence, these PEGylated insulin analogues of this invention are valuable for pulmonary administration.

The above-mentioned insulins that are stabilised towards proteolytic degradation are herein designated daughter insulins.

Via a suitable linker group, a PEG group can be attached to side chain(s) of lysine or cysteine residue(s) when present or attached to the N-terminal amino group(s) or at both places in the daughter insulin. The linker is typically a derivative of a carboxylic acid, where the carboxylic acid functionality is used for attachment to the daughter insulin via an amide bond. The linker may be an acetic acid moiety with the linking motif: —$CH_2CO$—, a propionic acid moiety with the linking motif: —$CH_2CH_2CO$— or —$CHCH_3CO$—, or a butyric acid moiety with the linking motif: —$CH_2CH_2CH_2CO$— or —$CH_2CHCH_3CO$—. Alternatively, the linker may be a —CO— group.

PEGylation of the lysine residue present in position B29 in the B-chain in the daughter insulin is desired. Furthermore, it is desirable that there is no Lys present in any of the positions 1 through 21 in the A chain (A1-A21) and no Lys present in any of the positions 1 through 28 in the B chain (B1-B28) in the daughter insulin. A preferred daughter insulin is an insulin having no B30 amino acid.

The daughter insulin molecule has a limited number of the naturally occurring amino acid residues substituted with other amino acid residues relative to human insulin as explained in the detailed part of the specification.

In one embodiment, this invention relates to a PEGylated insulin, wherein the daughter insulin analogue deviates from human insulin in one or more of the following deletions or substitutions: Q in position A18, A, G or Q in position A21, G or Q in position B1 or no amino acid residue in position B1, Q, S or T in position B3 or no amino acid residue in position B3, Q in position B13, no amino acid residue in position B27, D, E or R in position B28 and no amino acid in position B30.

The PEG group may vary in size within a large range as is well known within the art. However, too large PEG groups may interfere in a negative way with the biological activity of the PEGylated insulin molecule.

In still a further aspect, this invention is related to pharmaceutical preparations comprising the PEGylated insulin of this invention and suitable adjuvants and additives such as one or more agents suitable for stabilization, preservation or isotoni, e.g., zinc ions, phenol, cresol, a parabene, sodium chloride, glycerol or mannitol. The zinc content of the present formulations may be between 0 and about 6 zinc atoms per insulin hexamer. The pH value of the pharmaceutical preparation may be between about 4 and about 8.5, between about 4 and about 5 or between about 6.5 and about 7.5.

In a further embodiment, this invention is related to the use of the PEGylated insulin as a pharmaceutical for the reducing of blood glucose levels in mammalians, in particularly for the treatment of diabetes.

In a further aspect, this invention is related to the use of the PEGylated insulin for the preparation of a pharmaceutical preparation for the reducing of blood glucose level in mammalians, in particularly for the treatment of diabetes.

In a further embodiment, this invention is related to a method of reducing the blood glucose level in mammalians by administrating a therapeutically active dose of a PEGylated insulin of this invention to a patient in need of such treatment.

In a further aspect of this invention, the PEGylated insulins are administered in combination with one or more further active substances in any suitable ratios. Such further active agents may be selected from human insulin, fast acting insulin analogues, antidiabetic agents, antihyperlipidemic agents, antiobesity agents, antihypertensive agents and agents for the treatment of complications resulting from or associated with diabetes.

In one embodiment, the two active components are administered as a mixed pharmaceutical preparation. In another embodiment, the two components are administered separately either simultaneously or sequentially.

In one embodiment, the PEGylated insulins of this invention may be administered together with fast acting human insulin or human insulin analogues. Such fast acting insulin analogue may be such wherein the amino acid residue in position B28 is Asp, Lys, Leu, Val, or Ala and the amino acid residue in position B29 is Lys or Pro, des(B28-B30) human insulin, des(B27) human insulin or des(B30) human insulin, and an analogue wherein the amino acid residue in position B3 is Lys and the amino acid residue in position B29 is Glu or Asp. The PEGylated insulin of this invention and the rapid acting human insulin or human insulin analogue can be mixed in a ratio from about 90% of the PEGylated insulin to about 10% of the rapid acting human insulin or human insulin analogue; preferably from about 70% of the PEGylated insulin to about 30% of the rapid acting human insulin or human insulin analogue, and even more preferred from about 50% of the PEGylated insulin to about 50% of the rapid acting human insulin or human insulin analogue (% being weight percentage).

The PEGylated insulins of this invention may also be used on combination treatment together with an antidiabetic agent. Antidiabetic agents will include insulin, GLP-1 (1-37) (glucagon like peptide-1) described in WO 98/08871, WO 99/43706, U.S. Pat. No. 5,424,286 and WO 00/09666, GLP-2, exendin-4(1-39), insulinotropic fragments thereof, insulinotropic analogues thereof and insulinotropic derivatives thereof. Insulinotropic fragments of GLP1(1-37) are insulinotropic peptides for which the entire sequence can be found in the sequence of GLP1(1-37) and where at least one terminal amino acid has been deleted.

The PEGylated insulins of this invention may also be used on combination treatment together with an oral antidiabetic such as a thiazolidindione, metformin and other type 2 diabetic pharmaceutical preparation for oral treatment.

Furthermore, the PEGylated insulin of this invention may be administered in combination with one or more antiobesity agents or appetite regulating agents.

In one embodiment this invention is related to a pulmonal pharmaceutical preparation comprising the PEGgylated insulin of this invention and suitable adjuvants and additives such as one or more agents suitable for stabilization, preservation or isotoni, e.g., zinc ions, phenol, cresol, a parabene, sodium chloride, glycerol, propyleneglycol or mannitol.

It should be understood that any suitable combination of the PEGylated insulins with diet and/or exercise, one or more of the above-mentioned compounds and optionally one or more other active substances are considered to be within the scope of this invention.

DESCRIPTION OF THE PREFERRED EMBODIMENTS

Figure 1:
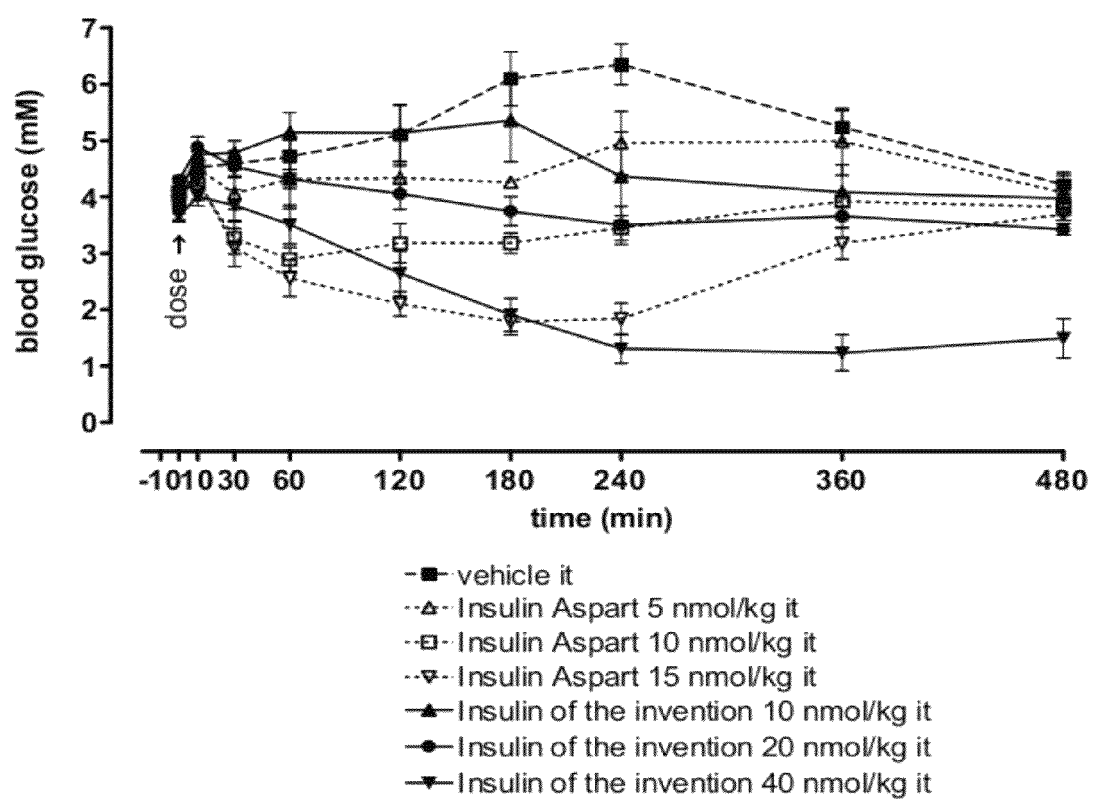
FIG. 1. is the blood glucose profile of the insulin of example 1 compared with insulin as part following intratracheal drop instillation in rats. The protocol is described in example 10. There were used 4-5 animals per group.

The stability and solubility properties of insulin are important underlying aspects for current insulin therapy. This invention is addressed to these issues by providing stable, PEGylated insulin analogues wherein the PEGylation decreases molecular flexibility and concomitantly reduce the fibrillation propensity and limit or modify the pH precipitation zone.

The PEGylated insulins of this invention are in particularly intended for pulmonary or oral administration due to their relatively high bioavailability compared to, e.g., human insulin and PEGylated human insulin. Furthermore, the PEGylated insulins will have a protracted insulin activity.

As mentioned above, insulins that are stabilised towards proteolytic degradation are herein designated daughter insulins. The PEGylated insulins of this invention are said daughter insulins which have been PEGylated as described herein.

Said daughter insulins are derived from insulin compounds which herein are designated parent insulins.

In one embodiment a parent insulin is selected from the group consisting of a) human insulin; b) an insulin analogue of human insulin wherein the amino acid residue in position B28 of is Pro, Asp, Lys, Leu, Val, or Ala and the amino acid residue in position B29 is Lys or Pro and optionally the amino acid residue in position B30 is deleted; c) an insulin analogue which is des(B28-B30) human insulin, des(B27) human insulin or des(B30) human insulin; d) an insulin analogue of human insulin wherein the amino acid residue in position B3 is Lys and the amino acid residue in position B29 is Glu or Asp; e) an insulin analogue of human insulin wherein the amino acid residue in position A21 is Gly and wherein the insulin analogue is further extended in the B-chain C-terminal with two arginine residues; and f) an insulin derivative wherein the amino acid residue in position B30 is substituted with a threonine methyl ester. Each of these groups is a specific embodiment.

In another embodiment, a parent insulin is selected from the group consisting of human insulin; desB30 human insulin; AspB28 human insulin; AspB28, DesB30 human insulin; LysB3, GluB29 human insulin; LysB28, ProB29 human insulin; GlyA21, ArgB31, ArgB32 human insulin; and desB30, ArgB31, ArgB32 human insulin.

More specifically, the daughter insulin is an insulin molecule having two or more mutations of the A and/or B chain relative to the parent insulin. Surprisingly, it has been found that by substituting two or more hydrophobic amino acids within or in close proximity to two or more protease sites on an insulin with hydrophilic amino acids, an insulin analogue (i.e., a daughter insulin) is obtained which is proteolytically more stable compared to the parent insulin. In a broad aspect, a daughter insulin is an insulin analogue wherein at least two hydrophobic amino acids have been substituted with hydrophilic amino acids relative to the parent insulin, wherein the substitutions are within or in close proximity to two or more protease cleavage sites of the parent insulin and wherein such insulin analogue optionally further comprises one or more additional mutations.

In another embodiment, a daughter insulin is an insulin analogue wherein
the amino acid in position A12 is Glu or Asp and/or the amino acid in position A13 is His, Asn, Glu or Asp and/or the amino acid in position A14 is Asn, Gln, Glu, Arg, Asp, Gly or His and/or the amino acid in position A15 is Glu or Asp; and
the amino acid in position B24 is His and or the amino acid in position B25 is His and/or the amino acid in position B26 is His, Gly, Asp or Thr and/or the amino acid in position B27 is His, Glu, Lys, Gly or Arg and/or the amino acid in position B28 is His, Gly or Asp; and
which optionally further comprises one or more additional mutations.

In another embodiment, a daughter insulin is an insulin analogue comprising an A-chain amino acid sequence of formula 1:

(SEQ ID No: 1)
Xaa$_{A(-2)}$-Xaa$_{A(-1)}$-Xaa$_{A0}$-Gly-Ile-Val-Glu-Gln-Cys-

Cys-Xaa$_{A8}$-Ser-Ile-Cys-Xaa$_{A12}$-Xaa$_{A13}$-Xaa$_{A14}$-

Xaa$_{A15}$-Leu-Glu-Xaa$_{A18}$-Tyr-Cys-Xaa$_{A21}$-Xaa$_{A22}$
Formula (1)

and a B-chain amino acid sequence of formula 2:

(SEQ ID No: 2)
Xaa$_{B(-2)}$-Xaa$_{B(-1)}$-Xaa$_{B0}$-Xaa$_{B1}$-Xaa$_{B2}$-Xaa$_{B3}$-Xaa$_{B4}$-

His-Leu-Cys-Gly-Ser-Xaa$_{B10}$-Leu-Val-Glu-Ala-Leu-

Xaa$_{B16}$-Leu-Val-Cys-Gly-Glu-Arg-Gly-Xaa$_{B24}$-Xaa$_{B25}$-

Xaa$_{B26}$-Xaa$_{B27}$-Xaa$_{B28}$-Xaa$_{B29}$-Xaa$_{B30}$-Xaa$_{B31}$-Xaa$_{B32}$
Formula (2)

wherein
Xaa$_{A(-2)}$ is absent or Gly;
Xaa$_{A(-1)}$ is absent or Pro;
Xaa$_{A0}$ is absent or Pro;
Xaa$_{A8}$ is independently selected from Thr and His;
Xaa$_{A12}$ is independently selected from Ser, Asp and Glu;
Xaa$_{A13}$ is independently selected from Leu, Thr, Asn, Asp, Gln, His, Lys, Gly, Arg, Pro, Ser and Glu;
Xaa$_{A14}$ is independently selected from Tyr, Thr, Asn, Asp, Gln, His, Lys, Gly, Arg, Pro, Ser and Glu;
Xaa$_{A15}$ is independently selected from Gln, Asp and Glu;
Xaa$_{A18}$ is independently selected from Asn, Lys and Gln;
Xaa$_{A21}$ is independently selected from Asn and Gln;
Xaa$_{A22}$ is absent or Lys;
Xaa$_{B(-2)}$ is absent or Gly;
Xaa$_{B(-1)}$ is absent or Pro;
Xaa$_{B0}$ is absent or Pro;
Xaa$_{B1}$ is absent or independently selected from Phe and Glu;
Xaa$_{B2}$ is absent or Val;
Xaa$_{B3}$ is absent or independently selected from Asn and Gln;
Xaa$_{B4}$ is independently selected from Gln and Glu;
Xaa$_{B10}$ is independently selected from His, Asp, Pro and Glu;
Xaa$_{B16}$ is independently selected from Tyr, Asp, Gln, His, Arg, and Glu;
Xaa$_{B24}$ is independently selected from Phe and His;
Xaa$_{B25}$ is independently selected from Phe and His;
Xaa$_{B26}$ is absent or independently selected from Tyr, His, Thr, Gly and Asp;
Xaa$_{B27}$ is absent or independently selected from Thr, Asn, Asp, Gln, His, Lys, Gly, Arg, Pro, Ser and Glu;
Xaa$_{B28}$ is absent or independently selected from Pro, His, Gly and Asp;
Xaa$_{B29}$ is absent or independently selected from Lys and Gln;
Xaa$_{B30}$ is absent or Thr;
Xaa$_{B31}$ is absent or Leu;
Xaa$_{B32}$ is absent or Glu;
the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge;
wherein optionally the N-terminal A-chain amino acid sequence is connected to the C-terminal B-chain amino acid sequence by an amino acid sequence comprising 3-7 amino acids to form a single chain insulin molecule, wherein optionally the N-terminal of the B-chain is extended with 1-10 amino acids;
wherein if Xaa$_{A8}$ is Thr and Xaa$_{A12}$ is Ser and Xaa$_{A13}$ is Leu and Xaa$_{A14}$ is Tyr then Xaa$_{A15}$ is Glu or Asp; and
wherein if Xaa$_{B24}$ is Phe and Xaa$_{B25}$ is Phe and Xaa$_{B26}$ is Tyr and Xaa$_{B27}$ is Thr and Xaa$_{B28}$ is Pro then Xaa$_{B29}$ Gln.

In another embodiment, a daughter insulin is an insulin analogue comprising an A-chain amino acid sequence of formula 3:

(SEQ ID No: 3)
```
Gly-Ile-Val-Glu-Gln-Cys-Cys-Xaa_A8-Ser-Ile-Cys-

Xaa_A12-Xaa_A13-Xaa_A14-Xaa_A15-Leu-Glu-Xaa_A18-Tyr-

Cys-Xaa_A21
Formula (3)
``` and a B-chain amino acid sequence of formula 4:

(SEQ ID No: 4)
```
Xaa_B1-Val-Xaa_B3-Xaa_B4-His-Leu-Cys-Gly-Ser-Xaa_B10-

Leu-Val-Glu-Ala-Leu-Xaa_B16-Leu-Val-Cys-Gly-Glu-

Arg-Gly-Xaa_B24-His-Xaa_B26-Xaa_B27-Xaa_B28-Xaa_B29-
Xaa_B30
Formula (4)
``` wherein
$Xaa_{A8}$ is independently selected from Thr and His;
$Xaa_{A12}$ is independently selected from Ser, Asp and Glu;
$Xaa_{A13}$ is independently selected from Leu, Thr, Asn, Asp, Gln, His, Lys, Gly, Arg, Pro, Ser and Glu;
$Xaa_{A14}$ is independently selected from Thr, Asn, Asp, Gln, His, Lys, Gly, Arg, Pro, Ser and Glu;
$Xaa_{A15}$ is independently selected from Gln, Asp and Glu;
$Xaa_{A18}$ is independently selected from Asn, Lys and Gln;
$Xaa_{A21}$ is independently selected from Asn, and Gln;
$Xaa_{B1}$ is independently selected from Phe and Glu;
$Xaa_{B3}$ is independently selected from Asn and Gln;
$Xaa_{B4}$ is independently selected from Gln and Glu;
$Xaa_{B10}$ is independently selected from His, Asp, Pro and Glu;
$Xaa_{B16}$ is independently selected from Tyr, Asp, Gln, His, Arg, and Glu;
$Xaa_{B24}$ is independently selected from Phe and His;
$Xaa_{B26}$ is absent or independently selected from Tyr, His, Thr, Gly and Asp;
$Xaa_{B27}$ is absent or independently selected from Thr, Asn, Asp, Gln, His, Lys, Gly, Arg, Pro, Ser and Glu;
$Xaa_{B28}$ is absent or independently selected from Pro, His, Gly and Asp;
$Xaa_{B29}$ is absent or independently selected from Lys and Gln;
$Xaa_{B30}$ is absent or Thr;
the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

In another embodiment, a daughter insulin is an insulin analogue
wherein
$Xaa_{A8}$ is independently selected from Thr and His;
$Xaa_{A12}$ is independently selected from Ser and Glu;
$Xaa_{A13}$ is independently selected from Leu, Thr, Asn, Asp, Gln, His, Lys, Gly, Arg, Pro, Ser and Glu;
$Xaa_{A14}$ is independently selected from Asp, His, and Glu;
$Xaa_{A15}$ is independently selected from Gln and Glu;
$Xaa_{A18}$ is independently selected from Asn, Lys and Gln;
$Xaa_{A21}$ is independently selected from Asn, and Gln;
$Xaa_{B1}$ is independently selected from Phe and Glu;
$Xaa_{B3}$ is independently selected from Asn and Gln;
$Xaa_{B4}$ is independently selected from Gln and Glu;
$Xaa_{B10}$ is independently selected from His, Asp, Pro and Glu;
$Xaa_{B16}$ is independently selected from Tyr, Asp, Gln, His, Arg, and Glu;
$Xaa_{B24}$ is independently selected from Phe and His;
$Xaa_{B26}$ is independently selected from Tyr, Thr, Gly and Asp;
$Xaa_{B27}$ is independently selected from Thr, Asn, Asp, Gln, His, Lys, Gly, Arg, and Glu;
$Xaa_{B28}$ is independently selected from Pro, Gly and Asp;
$Xaa_{B29}$ is independently selected from Lys and Gln;
$Xaa_{B30}$ is absent or Thr;
the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

Other embodiments of daughter insulins are mentioned below.

A "protease" or a "protease enzyme" is a digestive enzyme which degrades proteins and peptides and which is found in various tissues of the human body such as e.g. the stomach (pepsin), the intestinal lumen (chymotrypsin, trypsin, elastase, carboxypeptidases, etc.) or mucosal surfaces of the GI tract (aminopeptidases, carboxypeptidases, enteropeptidases, dipeptidyl peptidases, endopeptidases, etc.), the liver (Insulin degrading enzyme, cathepsin D etc), and in other tissues.

A proteolytically stable insulin analogue (also designated a daughter insulin) is herein to be understood as an insulin analogue, which is subjected to slower degradation by one or more proteases relative to human insulin. In one embodiment, a daughter insulin is subjected to slower degradation by one or more proteases relative to the parent insulin. In a further embodiment, a daughter insulin is stabilized against degradation by one or more enzymes selected from the group consisting of: pepsin (such as, e.g., the isoforms pepsin A, pepsin B, pepsin C and/or pepsin F), chymotrypsin (such as e.g. the isoforms chymotrypsin A, chymotrypsin B and/or chymotrypsin C), trypsin, Insulin-Degrading Enzyme (IDE), elastase (such as e.g. the isoforms pancreatic elastase I and/or II), carboxypeptidase (e.g. the isoforms carboxypeptidase A, carboxypeptidase A2 and/or carboxypeptidase B), aminopeptidase, cathepsin D and other enzymes present in intestinal extracts derived from rat, pig or human.

In one embodiment, a daughter insulin is stabilized against degradation by one or more enzymes selected from the group consisting of: chymotrypsin, trypsin, Insulin-Degrading Enzyme (IDE), elastase, carboxypeptidases, aminopeptidases and cathepsin D. In a further embodiment, a daughter insulin is stabilized against degradation by one or more enzymes selected from the group consisting of: chymotrypsin, carboxypeptidases and IDE. In a yet further embodiment, a daughter insulin is stabilized against degradation by one or more enzymes selected from: chymotrypsin and carboxypeptidases.

T½ may be determined as described in the Examples as a measure of the proteolytical stability of a daughter insulin towards protease enzymes such as chymotrypsin, pepsin and/or carboxypeptidase A. In one embodiment of the invention, T½ is increased relative to human insulin. In a further embodiment, T½ is increased relative to the parent insulin. In a yet further embodiment, T½ is increased at least 2-fold relative to the parent insulin. In a yet further embodiment, T½ is increased at least 3-fold relative to the parent insulin. In a yet further embodiment, T½ is increased at least 4-fold relative to the parent insulin. In a yet further embodiment, T½ is increased at least 5-fold relative to the parent insulin. In a yet further embodiment, T½ is increased at least 10-fold relative to the parent insulin.

Protease cleavage sites (herein also mentioned as protease sites) are to be understood as amino acid residues that are recognized by proteases and/or amino acid residues whose peptide bond is cleaved by proteases. Protease cleavage sites may be determined by determining cleavage "hot-spots" by HPLC, MS or LC-MS analyses and/or by prediction based on enzyme specificity of the protease enzyme for which the protease cleavage site is to be determined. A skilled person in the art will know how to determine protease cleavage sites for example based on enzyme specificities as for example described in Handbook of Proteolytical Enzymes, 2nd ed., Barrett, A. J., Rawlings, N. D., Woesner, J. F. editors, Elsevier Academic Press 2004. For example chymotrypsin is predicted to cleave peptide bonds C-terminal to aromatic residues (Trp, Tyr, Phe or Leu), that are not followed by Pro. Similarly, trypsin is predicted to cleave peptide bonds C-terminal to basic residues Lys or Arg, that are not followed by Pro, elastase is predicted to cleave residues C-terminal to Ala, Val, Gly or Ser and carboxypeptidase A will remove any C-terminal amino acid, but not Arg, Lys or Pro. Insulin-degrading enzyme (IDE) is predicted to cleave the following positions of human insulin B9-10, B10-11, B13-14, B14-15, B24-25, B25-26, A13-14 and A14-15.

The term substituting (an) amino acid "within or in close proximity" to a protease cleavage site is herein used to indicate the substitution of an amino acid within or in close proximity to a position of the parent insulin which has been determined to be a protease cleavage site. In one embodiment, two or more hydrophobic amino acids within or in close proximity to two or more protease sites on an insulin are substituted, wherein said hydrophobic amino acids are substituted with hydrophilic amino acids. In a further embodiment, two or more hydrophobic amino acids within two or more protease sites on an insulin are substituted with hydrophilic amino acids. In a yet further embodiment, two or more hydrophobic amino acids situated next to two or more protease sites on an insulin are substituted with hydrophilic amino acids. In a still further embodiment, two or more hydrophobic amino acids situated two amino acids away from to two or more protease sites on an insulin are substituted with hydrophilic amino acids. In a yet further embodiment, two or more hydrophobic amino acids situated three amino acids away from two or more protease sites on an insulin are substituted with hydrophilic amino acids. In a still further embodiment, two or more hydrophobic amino acids situated up to four amino acids away from two or more protease sites on an insulin are substituted with hydrophilic amino acids. In a yet further embodiment two or more hydrophobic amino acids situated one, two or three amino acids away from or within two or more protease sites on an insulin are substituted with hydrophilic amino acids. In a still further embodiment, two or more hydrophobic amino acids situated one or two amino acids away from or within two or more protease sites on an insulin are substituted with hydrophilic amino acids. In a yet further embodiment, two or more hydrophobic amino acids situated next to or within two or more protease sites on an insulin are substituted with hydrophilic amino acids.

A daughter insulin may have a net charge which is different than the net charge of the parent insulin. In one embodiment, the net charge of a daughter insulin is more positive than the net charge of the parent insulin. In one embodiment, the net charge of a daughter insulin is more negative than the net charge of the parent insulin. In one embodiment, the average positive net charge of a daughter insulin is between 0.5 and 5 as measured in an aqueous solution. In one embodiment, the average positive net charge of a daughter insulin is between 1 and 5. In one embodiment, the average positive net charge of a daughter insulin is between 1 and 4. In one embodiment, the average positive net charge of a daughter insulin is between 1 and 3. In one embodiment, the average positive net charge of a daughter insulin is between 2 and 3. In one embodiment, the average negative net charge of a daughter insulin is between −0.5 and −5 as measured in an aqueous solution. In one embodiment, the average negative net charge of a daughter insulin is between −1 and −5. In one embodiment, the average negative net charge of a daughter insulin is between −1 and −4. In one embodiment, the average negative net charge of a daughter insulin is between −1 and −3. In one embodiment, the average negative net charge of a daughter insulin is between −2 and −3.

In one embodiment, a daughter insulin may have increased solubility relative to human insulin. In a further embodiment, a daughter insulin has increased solubility relative to human insulin at pH 3-9. In a yet further embodiment, a daughter insulin has increased solubility relative to human insulin at pH 4-8.5. In a still further embodiment, a daughter insulin has increased solubility relative to human insulin at pH 4-8. In a yet further embodiment, a daughter insulin has increased solubility relative to human insulin at pH 4.5-8. In a further embodiment, a daughter insulin has increased solubility relative to human insulin at pH 5-8. In a yet further embodiment, a daughter insulin has increased solubility relative to human insulin at pH 5.5-8. In a further embodiment, a daughter insulin has increased solubility relative to human insulin at pH 6-8.

In one embodiment, a daughter insulin has increased solubility relative to human insulin at pH 2-4.

In one embodiment, a daughter insulin may have increased solubility relative to the parent insulin. In a further embodiment, a daughter insulin has increased solubility relative to the parent insulin at pH 3-9. In a yet further embodiment a daughter insulin has increased solubility relative to parent insulin at pH 4-8.5. In a still further embodiment, a daughter insulin has increased solubility relative to parent insulin at pH 4-8. In a yet further embodiment, a daughter insulin has increased solubility relative to parent insulin at pH 4.5-8. In a still further embodiment, a daughter insulin has increased solubility relative to parent insulin at pH 5-8. In a yet further embodiment, a daughter insulin has increased solubility relative to parent insulin at pH 5.5-8. In a further embodiment, a daughter insulin has increased solubility relative to parent insulin at pH 6-8.

In one embodiment, a daughter insulin has increased solubility relative to parent insulin at pH 2-4.

By "increased solubility at a given pH" is meant that a larger concentration of a daughter insulin dissolves in an aqueous or buffer solution at the pH of the solution relative to the parent insulin. Methods for determining whether the insulin contained in a solution is dissolved are known in the art.

In one embodiment, the solution may be subjected to centrifugation for 20 minutes at 30,000 g and then the insulin concentration in the supernatant may be determined by RP-HPLC. If this concentration is equal within experimental error to the insulin concentration originally used to make the composition, then the insulin is fully soluble in the composition of the invention. In another embodiment, the solubility of the insulin in a composition of the invention can simply be determined by examining by eye the container in which the composition is contained. The insulin is soluble if the solution is clear to the eye and no particulate matter is either suspended or precipitated on the sides/bottom of the container.

A daughter insulin may have increased potency and/or bioavalability relative to the parent insulin when compared upon measurement.

Standard assays for measuring insulin potency or bioavailability are known to the person skilled in the art and include inter alia (1) insulin radioreceptorassays, in which the relative potency of an insulin is defined as the ratio of insulin to insulin analogue required to displace 50% of $^{125}$I-insulin specifically bound to insulin receptors present on cell membranes, e.g. a rat liver plasma membrane fraction; (2) lipogenesis assays, performed e.g. with rat adipocytes, in which relative insulin potency is defined as the ratio of insulin to insulin analogue required to achieve 50% of the maximum conversion of [3-$^3$H] glucose into organic-extractable material (i.e. lipids); (3) glucose oxidation assays in isolated fat cells in which the relative potency of the insulin analogue is defined as the ratio of insulin to insulin analogue to achieve 50% of the maximum conversion of glucose-1-[$^{14}$C] into [$^{14}$CO$_2$]; (4) insulin radioimmunoassays which can determine the immunogenicity of insulin analogues by measuring the effectiveness by which insulin or an insulin analogue competes with $^{125}$I-insulin in binding to specific anti-insulin antibodies; and (5) other assays which measure the binding of insulin or an insulin analogue to antibodies in animal blood plasma samples, such as ELISA assays possessing specific insulin antibodies.

Daughter insulin may optionally be analyzed for further protease sites which may be subject to further substitutions of one or more hydrophobic amino acids with hydrophilic amino acids. A daughter insulin may be an insulin analogue which has at least two hydrophilic acids in protease sites compared to the parent insulin, the first modified insulin, and which has further at least one amino acid substitution in a new protease site of the first modified insulin wherein at least one hydrophobic amino acid has been substituted with at least one hydrophilic amino acid.

For the sake of convenience, here follows the names of codable, natural amino acids with the usual three letter codes & one letter codes in parenthesis: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (H is & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the insulins of this invention are, preferably, amino acids which can be coded for by a nucleic acid. In one embodiment insulin or an insulin analogue is substituted by Gly, Glu, Asp, His, Gin, Asn, Ser, Thr, Lys, Arg and/or Pro and/or Gly, Glu, Asp, His, Gin, Asn, Ser, Thr, Lys, Arg and/or Pro is added to insulin or an insulin analogue. In one embodiment insulin or an insulin analogue is substituted by Glu, Asp, His, Gin, Asn, Lys and/or Arg and/or Glu, Asp, His, Gin, Asn, Lys and/or Arg is added to insulin or an insulin analogue.

In one embodiment, a daughter insulin is selected from the group consisting of the following 123 compounds: A14E, B25H, desB30 human insulin; A14H, B25H, desB30 human insulin; A14E, B1E, B25H, desB30 human insulin; A14E, B16E, B25H, desB30 human insulin; A14E, B25H, B28D, desB30 human insulin; A14E, B25H, B27E, desB30 human insulin; A14E, B1E, B25H, B27E, desB30 human insulin; A14E, B1E, B16E, B25H, B27E, desB30 human insulin; A8H, A14E, B25H, desB30 human insulin; A8H, A14E, B25H, B27E, desB30 human insulin; A8H, A14E, B1E, B25H, desB30 human insulin; A8H, A14E, B1E, B25H, B27E, desB30 human insulin; A8H, A14E, B1E, B16E, B25H, B27E, desB30 human insulin; A8H, A14E, B16E, B25H, desB30 human insulin; A14E, B25H, B26D, desB30 human insulin; A14E, B1E, B27E, desB30 human insulin; A14E, B27E, desB30 human insulin; A14E, B28D, desB30 human insulin; A14D, B25H, desB30 human insulin; A(−1)P, A(0)P, A14E, B25H, desB30 human insulin; A14E, B(−1)P, B(0)P, B25H, desB30 human insulin; A(−1)P, A(0)P, A14E, B(−1)P, B(0)P, B25H, desB30 human insulin; A14E, B25H, B30T, B31L, B32E human insulin; A14E, B25H human insulin; A14E, B16H, B25H, desB30 human insulin; A14E, B10P, B25H, desB30 human insulin; A14E, B10E, B25H, desB30 human insulin; A14E, B4E, B25H, desB30 human insulin; A14H, B16H, B25H, desB30 human insulin; A14H, B10E, B25H, desB30 human insulin; A13H, A14E, B10E, B25H, desB30 human insulin; A13H, A14E, B25H, desB30 human insulin; A14E, A18Q, B3Q, B25H, desB30 human insulin; A14E, B24H, B25H, desB30 human insulin; A14E, B25H, B26G, B27G, B28G, desB30 human insulin; A14E, A18Q, A21Q, B3Q, B25H, desB30 human insulin; A14E, A18Q, A21Q, B3Q, B25H, B27E, desB30 human insulin; A14E, A18Q, B3Q, B25H, desB30 human insulin; A13H, A14E, B1E, B25H, desB30 human insulin; A13N, A14E, B25H, desB30 human insulin; A13N, A14E, B1E, B25H, desB30 human insulin; A(−2)G, A(−1)P, A(0)P, A14E, B25H, desB30 human insulin; A14E, B(−2)G, B(−1)P, B(0)P, B25H, desB30 human insulin; A(−2)G, A(−1)P, A(0)P, A14E, B(−2)G, B(−1)P, B(0)P, B25H, desB30 human insulin; A14E, B27R, B28D, B29K, desB30 human insulin; A14E, B25H, B27R, B28D, B29K, desB30 human insulin; A14E, B25H, B26T, B27R, B28D, B29K, desB30 human insulin; A14E, A22K, B25H, desB30 human insulin; A14E, B25H, B27R, desB30 human insulin; A14E, B25H, B27H, desB30 human insulin; A14E, A18Q, B3Q, B25H, desB30 human insulin; A13E, A14E, B25H, desB30 human insulin; A12E, A14E, B25H, desB30 human insulin; A15E, A14E, B25H, desB30 human insulin; A13E, B25H, desB30 human insulin; A12E, B25H, desB30 human insulin; A15E, B25H, desB30 human insulin; A14E, B25H, desB27, desB30 human insulin; A14E, B25H, B26D, B27E, desB30 human insulin; A14E, B25H, B27R, desB30 human insulin; A14E, B25H, B27N, desB30 human insulin; A14E, B25H, B27D, desB30 human insulin; A14E, B25H, B27Q, desB30 human insulin; A14E, B25H, B27E, desB30 human insulin; A14E, B25H, B27G, desB30 human insulin; A14E, B25H, B27H, desB30 human insulin; A14E, B25H, B27K, desB30 human insulin; A14E, B25H, B27P, desB30 human insulin; A14E, B25H, B27S, desB30 human insulin; A14E, B25H, B27T, desB30 human insulin; A13R, A14E, B25H, desB30 human insulin; A13N, A14E, B25H, desB30 human insulin; A13D, A14E, B25H, desB30 human insulin; A13Q, A14E, B25H, desB30 human insulin; A13E, A14E, B25H, desB30 human insulin; A13G, A14E, B25H, desB30 human insulin; A13H, A14E, B25H, desB30 human insulin; A13K, A14E, B25H, desB30 human insulin; A13P, A14E, B25H, desB30 human insulin; A13S, A14E, B25H, desB30 human insulin; A13T, A14E, B25H, desB30 human insulin; A14E, B16R, B25H, desB30 human insulin; A14E, B16D, B25H, desB30 human insulin; A14E, B16Q, B25H, desB30 human insulin; A14E, B16E, B25H, desB30 human insulin; A14E, B16H, B25H, desB30 human insulin; A14R, B25H, desB30 human insulin; A14N, B25H, desB30 human insulin; A14D, B25H, desB30 human insulin; A14Q, B25H, desB30 human insulin; A14E, B25H, desB30 human insulin; A14G, B25H, desB30 human insulin; A14H, B25H, desB30 human insulin; A8H, B10D, B25H human insulin; and A8H, A14E, B10E, B25H, desB30 human insulin.

Because virtually all PEG polymers are mixtures of many large molecules, one must resort to averages to describe molecular weight. Among many possible ways of reporting averages, three are commonly used: the number average, weight average, and z-average molecular weights. The weight average is probably the most useful of the three, because it fairly accounts for the contributions of different sized chains to the overall behaviour of the polymer, and correlates best with most of the physical properties of interest.

$$\text{Number average MW}(\overline{M}_n) \cdot \frac{\sum (M_i N_i)}{\sum (N_i)}$$

$$\text{Weight average MW}(\overline{M}_w) \cdot \frac{\sum (M_i^2 N_i)}{\sum (M_i N_i)}$$

$$Z \text{ average MW}(\overline{M}_z) \cdot \frac{\sum (M_i^3 N_i)}{\sum (M_i^2 N_i)}$$

where $N_i$ is the mole-fraction (or the number-fraction) of molecules with molecular weight $M_i$ in the polymer mixture. The ratio of $M_w$ to $M_n$ is known as the polydispersity index (PDI), and provides a rough indication of the breadth of the distribution. The PDI approaches 1.0 (the lower limit) for special polymers with very narrow MW distributions.

While lower molecular weight PEG groups may be preferred for increasing bioavailability, high molecular weight PEG chains, e.g., having an average molecular weight of 4000-6000 daltons or greater, although generally found to decrease the bioactivity of the insulin molecule, may be preferred for increasing half-life.

The PEG groups used in this invention will typically comprise a number of (—OCH$_2$CH$_2$—) subunits.

The PEG groups used in this invention will for a given molecular weight typically consist of a range of ethyleneglycol (or ethyleneoxide) monomers. For example, a PEG group of molecular weight 2000 dalton will typically consist of 43±10 monomers, the average being around 43-44 monomers, or 35-50 monomers.

The PEGylated insulins of this invention are mono-substituted having only one PEG group attached to a lysine amino acid residue in the daughter insulin molecule.

In this application, the PEGylated insulins are, to a great extent, named as if the linking moiety is a propionic acid linker, irrespective of the actual linker. In fact, within protein PEGylation literature, it is rarely specified which linking groups are used. The important variables are, with respect to biological properties: Size (in Daltons) and shape of the PEG moiety and position of the PEG attachment within the protein.

The daughter insulins are produced by expressing a DNA sequence encoding the insulin in question in a suitable host cell by well known technique as disclosed in, e.g., U.S. Pat. No. 6,500,645. The daughter insulin is either expressed directly or as a precursor molecule which has an N-terminal extension on the B-chain. This N-terminal extension may have the function of increasing the yield of the directly expressed product and may be of up to 15 amino acid residues long. The N-terminal extension is to be cleaved of in vitro after isolation from the culture broth and will therefore have a cleavage site next to B1. N-terminal extensions of the type suitable in this invention are disclosed in U.S. Pat. No. 5,395,922, and European Patent No. 765,395A.

The polynucleotide sequence coding for the daughter insulin may be prepared synthetically by established standard methods, e.g., the phosphoamidite method described by Beaucage et al. (1981) Tetrahedron Letters 22:1859-1869, or the method described by Matthes et al. (1984) EMBO Journal 3: 801-805. According to the phosphoamidite method, oligonucleotides are synthesized, e.g., in an automatic DNA synthesizer, purified, duplexed and ligated to form the synthetic DNA construct. A currently preferred way of preparing the DNA construct is by polymerase chain reaction (PCR).

The polynucleotide sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The recombinant method will typically make use of a vector which is capable of replicating in the selected microorganism or host cell and which carries a polynucleotide sequence encoding the daughter insulin. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector is capable of replicating in yeast. Examples of sequences which enable the vector to replicate in yeast are the yeast plasmid 2 μm replication genes REP 1-3 and origin of replication.

The vector may contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide sequence encoding the daughter insulin will also typically be operably connected to a suitable terminator. In yeast a suitable terminator is the TPI terminator (Alber et al. (1982) J. Mol. Appl. Genet. 1:419-434).

The procedures used to ligate the polynucleotide sequence encoding the daughter insulin, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulins of this invention, and subsequently inserting this fragment into a suitable expression vector, or by sequentially inserting DNA fragments containing genetic information for the individual elements (such as the signal, pro-peptide, connecting peptide, A and B chains) followed by ligation.

The vector comprising the polynucleotide sequence encoding the daughter insulin is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In one embodiment, the host cell is a yeast cell. The yeast organism may be any suitable yeast organism which, on cultivation, produces large amounts of the single chain insulin of the invention. Examples of suitable yeast organisms are strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted insulin, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g., ammonium sulphate, followed by purification by a variety of chromatographic procedures, e.g., ion exchange chromatography, affinity chromatography, or the like.

USE OF THE COMPOUNDS OF THIS INVENTION

The route of administration may be any route which effectively transports a compound of this invention to the desired or appropriate place in the body, such as parenterally, for example, subcutaneously, intramuscularly or intraveneously. Alternatively, a compound of this invention can be administered orally, pulmonary, or nasally.

For parenterally administration, a compound of this invention is formulated analogously with the formulation of known insulins. Furthermore, for parenterally administration, a compound of this invention is administered analogously with the administration of known insulins and the physicians are familiar with this procedure.

Parenteral administration can be performed by means of a syringe, optionally a pen-like syringe. Alternatively, parenteral administration can be performed by means of an infusion pump.

Injectable compositions containing a compound of this invention can be prepared using the conventional techniques of the pharmaceutical industry which involve dissolving and mixing the ingredients as appropriate to give the desired end product. Thus, according to one procedure, a compounds of this invention is dissolved in an amount of water which is somewhat less than the final volume of the composition to be prepared. An isotonic agent, a preservative and a buffer is added as required and the pH value of the solution is adjusted, if necessary, using an acid, for example, hydrochloric acid, or a base, for example, aqueous sodium hydroxide, as needed. Finally, the volume of the solution is adjusted with water to give the desired concentration of the ingredients.

More precisely, an insulin preparation of this invention, for example a solution or suspension, may be prepared by dissolving a compound of this invention in an aqueous medium at slightly acidic conditions, for example, in a concentration in the range from about 240 to about 1200 nmole/ml. The aqueous medium is made isotonic, for example, with sodium chloride or glycerol. Furthermore, the aqueous medium may contain zinc ions in a concentrations of up to about 20 µg of $Zn^{++}$ per unit of insulin activity, buffers such as acetate and citrate and preservatives such as m-cresol or phenol. The pH value of the solution is adjusted towards neutrality without getting too close to the isoelectric point of the compound of this invention in order to avoid precipitation. The pH value of the final insulin preparation depends upon which compound of this invention is used, the concentration of zinc ions and the concentration of the compound of this invention. The insulin preparation is made sterile, for example, by sterile filtration.

The insulin preparations of this invention are used similarly to the use of the known insulin preparations.

The amount of a compound of this invention to be administered, the determination of how frequently to administer a compound of this invention, and the election of which compound or compounds of this invention to administer, optionally together with another antidiabetic compound, is decided in consultation with a practitioner who is familiar with the treatment of diabetes. Hence, this invention also relates to a method of treating diabetes, comprising administering an affective amount of a compound of this invention to a patient in need of such treatment.

PHARMACEUTICAL COMPOSITIONS

The PEGylated insulins of this invention may be administered subcutaneously, nasally, orally, or pulmonary.

For subcutaneous administration, the PEGylated insulins of this invention are formulated analogously with the formulation of known insulins. Furthermore, for subcutaneous administration, the PEGylated insulins of this invention are administered analogously with the administration of known insulins and, generally, the physicians are familiar with this procedure.

PEGylated insulins of this invention may be administered by inhalation in a dose effective to increase circulating insulin levels and/or to lower circulating glucose levels. Such administration can be effective for treating disorders such as diabetes or hyperglycemia. Achieving effective doses of insulin requires administration of an inhaled dose of more than about 0.5 µg/kg to about 50 µg/kg of PEGylated insulins of this invention. A therapeutically effective amount can be determined by a knowledgeable practitioner, who will take into account factors including insulin level, blood glucose levels, the physical condition of the patient, the patient's pulmonary status, or the like.

The PEGylated insulins of this invention may be delivered by inhalation to achieve slow absorption and/or reduced systemical clearance thereof. Different inhalation devices typically provide similar pharmacokinetics when similar particle sizes and similar levels of lung deposition are compared.

The PEGylated insulins of this invention may be delivered by any of a variety of inhalation devices known in the art for administration of a therapeutic agent by inhalation. These devices include metered dose inhalers, nebulizers, dry powder generators, sprayers, and the like. Preferably, the PEGylated insulins of this are delivered by a dry powder inhaler or a sprayer. There are a several desirable features of an inhalation device for administering PEGylated insulins of this invention. For example, delivery by the inhalation device is advantageously reliable, reproducible, and accurate. The inhalation device should deliver small particles or aerosols, e.g., less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of PEGylated insulins of this invention, the quantity of the formulation delivered and the duration of administration of a single dose depend on the type of inhalation device employed. For some aerosol delivery systems, such as nebulizers, the frequency of administration and length of time for which the system is activated will depend mainly on the concentration of PEGylated insulins in the aerosol. For example, shorter periods of administration can be used at higher concentrations of PEGylated insulins in the nebulizer solution. Devices such as metered dose inhalers can produce higher aerosol concentrations, and can be operated for shorter periods to deliver the desired amount of the PEGylated insulins. Devices such as powder inhalers deliver active agent until a given charge of agent is expelled from the device. In this type of inhaler, the amount of insulin PEGylated insulins of this invention in a given quantity of the powder determines the dose delivered in a single administration.

The particle size of PEGylated insulins of this invention in the formulation delivered by the inhalation device is critical with respect to the ability of insulin to make it into the lungs, and preferably into the lower airways or alveoli. Preferably, the PEGylated insulins of this invention ion is formulated so that at least about 10% of the PEGylated insulins delivered is deposited in the lung, preferably about 10 to about 20%, or more. It is known that the maximum efficiency of pulmonary deposition for mouth breathing humans is obtained with particle sizes of about 2 µm to about 3 µm. When particle sizes are above about 5 µm, pulmonary deposition decreases substantially. Particle sizes below about 1 µm cause pulmonary deposition to decrease, and it becomes difficult to deliver particles with sufficient mass to be therapeutically effective. Thus, particles of the PEGylated insulins delivered by inhalation have a particle size preferably less than about 10 µm, more preferably in the range of about 1 µm to about 5 µm. The formulation of the PEGylated insulins is selected to yield the desired particle size in the chosen inhalation device.

Advantageously for administration as a dry powder a PEGylated insulin of this invention is prepared in a particulate form with a particle size of less than about 10 µm, preferably about 1 to about 5 µm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 µm. Such formulations can be achieved by spray drying, milling, or critical point condensation of a solution containing the PEGylated insulin of this invention and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of PEGylated insulins of this invention for administration from a dry powder inhaler typically include a finely divided dry powder containing the derivative, but the powder can also include a bulking agent, carrier, excipient, another additive, or the like. Additives can be included in a dry powder formulation of PEGylated insulin, e.g., to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The PEGylated insulin can be mixed with an additive at a molecular level or the solid formulation can include particles of the PEGylated insulin mixed with or coated on particles of the additive. Typical additives include mono-, di-, and polysaccharides; sugar alcohols and other polyols, such as, e.g., lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the PEGylated insulins of this invention can be produced by forcing a suspension or solution of the PEGylated insulin through a nozzle under pressure. The nozzle size and configuration, the applied pressure, and the liquid feed rate can be chosen to achieve the desired output and particle size. An electrospray can be produced, e.g., by an electric field in connection with a capillary or nozzle feed. Advantageously, particles of insulin conjugate delivered by a sprayer have a particle size less than about 10 µm, preferably in the range of about 1 µm to about 5 µm.

Formulations of PEGylated insulins of this invention suitable for use with a sprayer will typically include the PEGylated insulins in an aqueous solution at a concentration of from about 1 mg to about 500 mg of the PEGylated insulin per ml of solution. Depending on the PEGylated insulin chosen and other factors known to the medical advisor, the upper limit may be lower, e.g., 450, 400, 350, 300, 250, 200, 150, 120, 100 or 50 mg of the PEGylated insulin per ml of solution. The formulation can include agents such as an excipient, a buffer, an isotonicity agent, a preservative, a surfactant, and, preferably, zinc. The formulation can also include an excipient or agent for stabilization of the PEGylated insulin, such as a buffer, a reducing agent, a bulk protein, or a carbohydrate. Bulk proteins useful in formulating insulin conjugates include albumin, protamine, or the like. Typical carbohydrates useful in formulating the PEGylated insulin include sucrose, mannitol, lactose, trehalose, glucose, or the like. The PEGylated insulins formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing a PEGylated insulin of this invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump.

Injectable compositions of the PEGylated insulins of this invention can be prepared using the conventional techniques of the pharmaceutical industry which involve dissolving and mixing the ingredients as appropriate to give the desired end product. Thus, according to one procedure, a PEGylated insulin is dissolved in an amount of water which is somewhat less than the final volume of the composition to be prepared. Zink, an isotonic agent, a preservative and/or a buffer is/are added as required and the pH value of the solution is adjusted—if necessary—using an acid, e.g., hydrochloric acid, or a base, e.g., aqueous sodium hydroxide as needed. Finally, the volume of the solution is adjusted with water to give the desired concentration of the ingredients.

In a further embodiment of this invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of this invention.

In a further embodiment of this invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)-1,2-propanediol) or mixtures thereof. In a further embodiment of this invention the preservative is present in a concentration from about 0.1 mg/ml to 20 mg/ml. In a further embodiment of this invention the preservative is present in a concentration from about 0.1 mg/ml to 5 mg/ml. In a further embodiment of this invention the preservative is present in a concentration from about 5 mg/ml to 10 mg/ml. In a further embodiment of this invention the preservative is present in a concentration from about 10 mg/ml to 20 mg/ml. Each one of these specific preservatives constitutes an alternative embodiment of this invention. The use of a preservative in pharmaceutical compositions is well-known to the skilled person. For convenience reference is made to Remington: *The Science and Practice of Pharmacy,* $19^{th}$ edition, 1995.

In a further embodiment of this invention, the formulation further comprises an isotonic agent which may be selected from the group consisting of a salt (e.g., sodium chloride), a sugar or sugar alcohol, an amino acid (for example, L-glycine, L-histidine, arginine, lysine, isoleucine, aspartic acid, tryptophan or threonine), an alditol (e.g. glycerol (glycerine), 1,2-propanediol (propyleneglycol), 1,3-propanediol or 1,3-butanediol), polyethyleneglycol (e.g., PEG400) or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, e.g., mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of this invention. In one embodiment, the sugar or sugar alcohol concentration is between about 1 mg/ml and about 150 mg/ml. In a further embodiment of this invention the isotonic agent is present in a concentration from about 1 mg/ml to 50 mg/ml. In a further embodiment of this invention the isotonic agent is present in a concentration from about 1 mg/ml to 7 mg/ml. In a further embodiment of this invention the isotonic agent is present in a concentration from about 8 mg/ml to 24 mg/ml. In a further embodiment of this invention the isotonic agent is present in a concentration from about 25 mg/ml to 50 mg/ml. Each one of these specific isotonic agents constitutes an alternative embodiment of this invention. The use of an isotonic agent in pharmaceutical compositions is well-known to the skilled person. For convenience reference is made to Remington: *The Science and Practice of Pharmacy,* $19^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of a PEGylated insulins of this invention may, e.g., be prepared as described in European Patent No. 272,097.

Compositions containing PEGylated insulins of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the PEGylated insulin of this invention be determined for each individual patient by those skilled in the art in a similar way as for known insulin compositions.

PREFERRED FEATURES OF THIS INVENTION

The features of this invention are as follows:
1. A PEGylated insulin analogue wherein, in the daughter insulin, at least two hydrophobic amino acids have been substituted with hydrophilic amino acids relative to the parent insulin, wherein the substitutions are within or in close proximity to two or more protease cleavage sites of the parent insulin and wherein such daughter insulin optionally further comprises one or more additional mutations, and wherein the PEG moiety, via a linker, is attached to the $\epsilon$ amino group of the lysine residue in position B29 in said daughter insulin.
2. A PEGylated insulin analogue according to clause 1 wherein the daughter insulin has increased solubility relative to the parent insulin,
3. A PEGylated insulin analogue according to any one of the preceding clauses wherein the A-chain of the insulin analogue comprises at least one mutation and the B-chain of the insulin analogue comprises at least one mutation relative to the parent insulin.
4. A PEGylated insulin analogue according to any one of the preceding clauses wherein the insulin analogue further comprises at least one amino acid substitution in a protease site of a first modified insulin analogue, wherein said at least one amino acid substitution is such that at least one hydrophobic amino acid has been substituted with at least one hydrophilic amino acid.
5. A PEGylated insulin analogue according to any of the preceding clauses wherein the amino acid in position A12 is Glu or Asp; and/or the amino acid in position A13 is His, Asn, Glu or Asp; and/or the amino acid in position A14 is Asn, Gln, Glu, Arg, Asp, Gly or His; and/or the amino acid in position A15 is Glu or Asp; and the amino acid in position B24 is His; and/or the amino acid in position B25 is His; and/or the amino acid in position B26 is His, Gly, Asp or Thr; and/or the amino acid in position B27 is His, Glu, Lys, Gly or Arg; and/or the amino acid in position B28 is His, Gly or Asp; and which optionally further comprises one or more additional mutations.
6. A PEGylated insulin analogue according to any of the preceding clauses wherein the amino acid in position A14 is Glu, Asp or His, the amino acid in position B25 is His and which optionally further comprises one or more additional mutations.
7. A PEGylated insulin analogue according to any of the preceding clauses wherein the amino acid in position A14 is Glu, Asp or His, the amino acid in position B25 is His and the amino acid in position B30 is deleted.
8. A PEGylated insulin analogue according to any of the preceding clauses wherein the amino acid in position A14 is Glu, Asp or His and the amino acid in position B25 is His.
9. A PEGylated insulin analogue according to any of the preceding clauses to the extent possible wherein the one or more additional mutations is selected from a group consisting of: A(-3)Gly, A(-2)Gly, A(-1)Pro, A(0)Pro, A8His, A18Gln, A18Gln, A21Gln, A21Gly, B(-3)Gly, B(-2)Gly, B(-1)Pro, B(0)Pro, B1Glu, B1Gln, ro, B1Glu, B1Gln, B3Gln, B10Pro, B14Thr, B16Glu, B17Ser, B26Asp, DesB26, DesB27, B27Glu, B27Glu, B28Asp, desB28, desB29, desB30, B31Leu, B32Glu.
10. A PEGylated insulin analogue according to any of the preceding clauses to the extent possible wherein the additional mutation is desB30.
11. A PEGylated insulin analogue according to any the preceding clauses to the extent possible wherein A14 is Glu.
12. A PEGylated insulin analogue according to any of the preceding clauses to the extent possible which shows increased stability towards one or more protease enzymes relative to the parent protein.
13. A PEGylated insulin analogue according to any of the preceding clauses to the extent possible which shows increased stability towards two or more protease enzymes relative to the parent protein.
14. A PEGylated insulin analogue according to any of the preceding clauses to the extent possible wherein the parent insulin is selected from a group consisting of a) human insulin; b) an insulin analogue of human insulin wherein the amino acid residue in position B28 is Pro, Asp, Lys, Leu, Val or Ala and the amino acid residue in position B29 is Lys or Pro and optionally the amino acid residue in position B30 is deleted; c) des(B26-B30) human insulin, des(B27-B30) human insulin, des(B28-B30) human insulin, des(B29-B30) human insulin, des(B27) human insulin or des(B30) human insulin; d) an insulin analogue of human insulin wherein the amino acid residue in position B3 is Lys and the amino acid residue in position B29 is Glu or Asp; e) an insulin analogue of human insulin wherein the amino acid residue in position A21 is Gly and wherein the insulin analogue is further extended in the B-chain C-terminal with two Arg residues; and f) an insulin derivative wherein the amino acid residue in position B30 is substituted with a threonine methyl ester.
15. A PEGylated insulin analogue according to any of the preceding clauses to the extent possible wherein the one or more additional mutations are selected to enhance chemical stability of insulin.
16. A PEGylated insulin analogue according to the preceding clause wherein the one or more additional mutations are selected from a group consisting of A18Gln, A21Gln, A21GLy and B3Gln.
17. A PEGylated insulin analogue according to any of the preceding clauses to the extent possible comprising an A-chain amino acid sequence of formula 1 $Xaa_{A(-2)}$-$Xaa_{A(-1)}$-$Xaa_{A0}$-Gly-Ile-Val-Glu-Gln-Cys-Cys-$Xaa_{A8}$-Ser-Ile-Cys-$Xaa_{A12}$-$Xaa_{A13}$-$Xaa_{A14}$-$Xaa_{A15}$-Leu-Glu-$Xaa_{A18}$-Tyr-Cys-$Xaa_{A21}$-$Xaa_{A22}$ (SEQ ID No:1) and a B-chain amino acid sequence of formula 2 $Xaa_{B(-2)}$-$Xaa_{B(-1)}$-$Xaa_{B0}$-$Xaa_{B1}$-$Xaa_{B2}$-$Xaa_{B3}$-$Xaa_{B4}$-His-Leu-Cys-Gly-Ser-$Xaa_{B10}$-Leu-Val-Glu-Ala-Leu-$Xaa_{B16}$-Leu-Val-Cys-Gly-Glu-Arg-Gly-$Xaa_{B24}$-$Xaa_{B25}$-$Xaa_{B26}$-$Xaa_{B27}$-$Xaa_{B28}$-$Xaa_{B29}$-$Xaa_{B30}$-$Xaa_{B31}$-$Xaa_{B32}$ (SEQ ID No:2) wherein $Xaa_{A(-2)}$ is absent or Gly; $Xaa_{A(-1)}$ is absent or Pro; $Xaa_{A0}$ is absent or Pro; $Xaa_{A8}$ is independently selected from Thr and His; $Xaa_{A12}$ is independently selected from Ser, Asp and Glu; $Xaa_{A13}$ is independently selected from Leu, Thr, Asn, Asp, Gln, His, Lys, Gly, Arg, Pro, Ser and Glu; $Xaa_{A14}$ is independently selected from Tyr, Thr, Asn, Asp, Gln, His, Lys, Gly, Arg, Pro, Ser and Glu; $Xaa_{Am}$ is independently selected from Gln, Asp and Glu; $Xaa_{A18}$ is independently selected from Asn, Lys and Gln; $Xaa_{A21}$ is independently selected from Asn and Gln; $Xaa_{A22}$ is absent or Lys; $Xaa_{B(-2)}$ is absent or Gly; $Xaa_{B(-1)}$ is absent or Pro; $Xaa_{B0}$ is absent or Pro; $Xaa_{B1}$ is absent or independently selected from Phe and Glu; $Xaa_{B2}$ is absent or Val; $Xaa_{B3}$ is absent or independently selected from Asn and Gln; $Xaa_{B4}$ is independently selected from Gln and Glu; $Xaa_{B10}$ is independently selected from His, Asp, Pro and Glu; $Xaa_{B16}$ is independently selected from Tyr, Asp, Gln, His, Arg, and Glu; $Xaa_{B24}$ is independently selected from Phe and His; $Xaa_{B25}$ is independently selected from Phe and His; $Xaa_{B26}$ is absent or independently selected from Tyr, His, Thr, Gly and Asp; $Xaa_{B27}$ is absent or independently selected from Thr, Asn, Asp, Gln, His, Lys, Gly, Arg, Pro, Ser and Glu; $Xaa_{B28}$ is absent or independently selected from Pro, His, Gly and Asp; $Xaa_{B29}$ is absent or independently selected from Lys and Gln; $Xaa_{B30}$ is absent or Thr; $Xaa_{B31}$ is absent or Leu; $Xaa_{B32}$ is absent or Glu; the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge; wherein optionally the N-terminal A-chain amino acid sequence is connected to the C-terminal B-chain amino acid sequence by an amino acid sequence comprising 3-7 amino acids to form a single chain insulin molecule, wherein optionally the N-terminal of the B-chain is extended with 1-10 amino acids; wherein if $Xaa_{A8}$ is Thr and $Xaa_{A12}$ is Ser and $Xaa_{A13}$ is Leu and $Xaa_{A14}$ is Tyr then $Xaa_{A15}$ is Glu or Asp; and wherein if $Xaa_{B24}$ is Phe and $Xaa_{B25}$ is Phe and $Xaa_{B26}$ is Tyr and $Xaa_{B27}$ is Thr and $Xaa_{B28}$ is Pro then $Xaa_{B29}$ Gln.

18. A PEGylated insulin analogue according to any of the preceding clauses to the extent possible comprising an A-chain amino acid sequence of formula 3 Gly-Ile-Val-Glu-Gln-Cys-Cys-$Xaa_{A8}$-Ser-Ile-Cys-$Xaa_{A12}$-$Xaa_{A13}$-$Xaa_{A14}$-$Xaa_{A15}$-Leu-Glu-$Xaa_{A18}$-Tyr-Cys-$Xaa_{A21}$ (SEQ ID No:3) and a B-chain amino acid sequence of formula 4 $Xaa_{B1}$-Val-$Xaa_{B3}$-$Xaa_{B4}$-His-Leu-Cys-Gly-Ser-$Xaa_{B10}$-Leu-Val-Glu-Ala-Leu-$Xaa_{B16}$-Leu-Val-Cys-Gly-Glu-Arg-Gly-$Xaa_{B24}$-His-$Xaa_{B26}$-$Xaa_{B27}$-$Xaa_{B28}$-$Xaa_{B29}$-$Xaa_{B30}$ (SEQ ID No:4) wherein $Xaa_{A8}$ is independently selected from Thr and His; $Xaa_{A12}$ is independently selected from Ser, Asp and Glu; $Xaa_{A13}$ is independently selected from Leu, Thr, Asn, Asp, Gln, His, Lys, Gly, Arg, Pro, Ser and Glu; $Xaa_{A14}$ is independently selected from Thr, Asn, Asp, Gln, His, Lys, Gly, Arg, Pro, Ser and Glu; $Xaa_{A15}$ is independently selected from Gln, Asp and Glu; $Xaa_{A18}$ is independently selected from Asn, Lys and Gln; $Xaa_{A21}$ is independently selected from Asn, and Gln; $Xaa_{B1}$ is independently selected from Phe and Glu; $Xaa_{B3}$ is independently selected from Asn and Gln; $Xaa_{B4}$ is independently selected from Gln and Glu; $Xaa_{B10}$ is independently selected from His, Asp, Pro and Glu; $Xaa_{B16}$ is independently selected from Tyr, Asp, Gln, His, Arg, and Glu; $Xaa_{B24}$ is independently selected from Phe and His; $Xaa_{B26}$ is absent or independently selected from Tyr, His, Thr, Gly and Asp; $Xaa_{B27}$ is absent or independently selected from Thr, Asn, Asp, Gln, His, Lys, Gly, Arg, Pro, Ser and Glu; $Xaa_{B28}$ is absent or independently selected from Pro, His, Gly and Asp; $Xaa_{B29}$ is absent or independently selected from Lys and Gln; $Xaa_{B38}$ is absent or Thr; the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

19. A PEGylated insulin analogue according to the preceding clause, wherein $Xaa_{A8}$ is independently selected from Thr and His; $Xaa_{A12}$ is independently selected from Ser and Glu; $Xaa_{A13}$ is independently selected from Leu, Thr, Asn, Asp, Gln, His, Lys, Gly, Arg, Pro, Ser and Glu; $Xaa_{A14}$ is independently selected from Asp, His, and Glu; $Xaa_{A18}$ is independently selected from Gln and Glu; $Xaa_{A18}$ is independently selected from Asn, Lys and Gln; $Xaa_{A21}$ is independently selected from Asn, and Gln; $Xaa_{B1}$ is independently selected from Phe and Glu; $Xaa_{B3}$ is independently selected from Asn and Gln; $Xaa_{B4}$ is independently selected from Gln and Glu; $Xaa_{B18}$ is independently selected from His, Asp, Pro and Glu; $Xaa_{B16}$ is independently selected from Tyr, Asp, Gln, His, Arg, and Glu; $Xaa_{B24}$ is independently selected from Phe and His; $Xaa_{B26}$ is independently selected from Tyr, Thr, Gly and Asp; $Xaa_{B27}$ is independently selected from Thr, Asn, Asp, Gln, His, Lys, Gly, Arg, and Glu; $Xaa_{B28}$ is independently selected from Pro, Gly and Asp; $Xaa_{B29}$ is independently selected from Lys and Gln; $Xaa_{B38}$ is absent or Thr; the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

20. A PEGylated insulin analogue wherein, in the daughter insulin, the amino acid in position A14 is Glu or His (i.e., E and H, according to the one letter code), the amino acid in position B25 is His and which optionally further comprises one or more additional mutations, and wherein the PEG moiety, via a linker, is attached to the ε amino acid in the lysine residue in position B29.

21. A PEGylated insulin analogue according to the preceding clause wherein the daughter insulin comprises the A14E mutation.

22. A PEGylated insulin analogue according to any one of the preceding clauses to the extent possible wherein, in the daughter insulin, apart from the mutation in position B25, there is only the mutation in position A14 mentioned in the preceding clause.

23. A PEGylated insulin analogue according to clause 21 wherein the daughter insulin comprises the A14H mutation.

24. A PEGylated insulin analogue according to any one of the preceding clauses to the extent possible wherein the daughter insulin analogue comprises the desB30 mutation.

25. A PEGylated insulin analogue according to any of the preceding clauses to the extent possible wherein the one or more additional mutations within the daughter insulin is selected from a group consisting of: A(−1)P, A(0)P, A8H, A21G, B(−1)P, B(0)P, B1E, B1Q, B16E, B26D, B27E, B28D, desB30, B31L, B32E.
26. A PEGylated insulin analogue according to the preceding clause, wherein the daughter insulin, apart from the mutations in positions A14 and B25, has only one of the mutations mentioned in the previous clauses.
27. A PEGylated insulin analogue according to any one of the preceding clauses but the last one (i.e. except clause 27) to the extent possible, wherein the daughter insulin, apart from the mutations in positions A14 and B25, has exactly two of the mutations mentioned in the preceding clause but one (i.e., mentioned in clause 25).
28. A PEGylated insulin analogue according to any one of the preceding clauses but the last two (i.e. except clauses 26 and 27) to the extent possible, wherein the daughter insulin, apart from the mutations in positions A14 and B25, has exactly three of the mutations mentioned in the preceding clause but two (i.e., mentioned in clause 25).
29. A PEGylated insulin analogue according to any one of the preceding clauses but the last two (i.e. except clauses 27 and 28) to the extent possible wherein, apart from the mutations in positions A14 and B25, the only additional mutation is desB30.
30. A PEGylated insulin analogue, according to any one of the preceding clauses, comprising the moiety —($OCH_2CH_2$)$_n$—, wherein n is in integer in the range from 2 to about 1000, preferably from 2 to about 500, preferably from 2 to about 250, preferably from 2 to about 125, preferably from 2 to about 50, preferably from 2 to about 25, and preferably from 2 to about 12.
31. A PEGylated insulin analogue, according to any one of the preceding, possible clauses, wherein the polyethylene glycol moiety has a nominal molecular weight in the range from about 200 to about 40,000, preferably from about 200 to about 30,000, preferably from about 200 to about 20,000, preferably from about 200 to about 10,000, preferably from about 200 to about 5,000, preferably from about 200 to about 2,000, preferably from about 200 to about 1,000, and preferably from about 200 to about 750.
32. A PEGylated insulin analogue, according to any one of the preceding, possible clauses, wherein the polyethylene glycol moiety is monodisperse.
33. A PEGylated insulin analogue, according to the preceding clause, wherein the polyethylene glycol moiety has the general formula —($CH_2CH_2O$)$_n$—, wherein n is in an integer which is at least about 6, preferably at least about 10, and not more than about 110, preferably not more than about 75, and even more preferred n is in the range from about 6 to about 30, preferably in the range from about 10 to about 48.
34. A PEGylated insulin analogue, according to any one of the preceding possible clauses, wherein the polyethylene glycol moiety is polydisperse.
35. A PEGylated insulin analogue, according to any one of the preceding, possible clauses, wherein the polyethylene glycol moiety is linear, branched, forked or dumbbell shaped.
36. A PEGylated insulin analogue, according to any one of the preceding, possible clauses, comprising a group of the general formula -$Q^1$-($OCH_2CH_2$)$_n$—$R^1$, wherein $Q^1$ is a linker connecting the polyethylene glycol moiety to an ε-NH-group of an amino acid in the daughter insulin, preferably via an amide or a carbamate bond, n is an integer in the range from 2 to about 1000, and $R^1$ is alkoxy or hydroxyl, preferably methoxy.
37. A PEGylated insulin analogue, according to the preceding clause, wherein n is an integer in the range from 2 to about 500, preferably from 2 to about 500, preferably from 2 to about 250, preferably from 2 to about 125, preferably from 2 to about 50, and preferably from 2 to about 25.
38. A PEGylated insulin analogue, according to any one of the preceding, possible clauses, wherein $Q^1$ is -alkylene-CO—, which is connected to the —NH— residue of the insulin via the carbonyl group.
39. A PEGylated insulin analogue, according to the preceding clause, wherein $Q^1$ is ethylene carbonyl (—($CH_2$)$_2$—CO—), which is connected to the —NH— residue via the carbonyl group.
40. A PEGylated insulin analogue, according to any one of the preceding, possible clauses except the two last, wherein $Q^1$ is -alkylene-NHCO-alkylene-CO—, which is connected to the —NH— residue of the insulin via the carbonyl group.
41. A PEGylated insulin analogue, according to any one of the preceding, possible clauses except the three last, wherein $Q^1$ is —CO-alkylene-CO—.
42. A PEGylated insulin analogue, according to any one of the preceding, possible clauses except the four last, wherein $Q^1$ is —CO—.
43. A PEGylated insulin analogue, according to any one of the preceding, possible clauses except the five last, wherein $Q^1$ is (-alkylene-NHCO-alkylene-O-alkylene-)$_p$$CH_q$—NHCO-alkylene-($OCH_2CH_2$)$_r$—NHCO-alkylene-CO—, wherein p is 1, 2 or 3, q is 0, 1 or 2, p+q is 3, and r is an integer in the range from 1 to about 12, which is connected to the —NH— residue of the insulin via the carbonyl group.
44. A PEGylated insulin analogue, according to any on of the preceding, possible clauses, wherein $Q^1$ is —$CH_2CO$—, —$CH_2CH_2CO$—, —$CH_2CH_2CH_2CO$—, —$CH_2CH(CH_3)CO$—, —$CH_2CH_2CH_2CH_2CO$—, —$CH_2CH_2CH(CH_3)CO$—, —$CH_2CH_2CH_2CH_2CH_2CO$—, —$CH_2CH_2NH$—$COCH_2CH_2CO$—, —$CH_2CH_2NH$—$COCH_2CH_2CH_2CO$—, —$CH_2CH_2CH_2NH$—$COCH_2CH_2CO$—, —$CH_2CH_2CH_2NH$—$COCH_2CH_2CH_2CO$—, —$COCH_2CH_2CO$—, —$COCH_2CH_2CH_2CO$—, —CO—, (—$CH_2CH_2NHCOCH_2CH_2OCH_2$)$_3$$CNH$—$COCH_2CH_2$($OCH_2CH_2$)$_4$$NHCOCH_2CH_2CO$— or (—$CH_2CH_2NHCOCH_2CH_2OCH_2$)$_3$$CNH$—$COCH_2CH_2$($OCH_2CH_2$)$_4$$NHCOCH_2CH_2CH_2CO$—.
45. A PEGylated insulin analogue, according to any one of the preceding, possible clauses, wherein $R^1$ is alkoxy.
46. A PEGylated insulin analogue, according to the preceding clause, wherein $R^1$ is methoxy.
47. A compound according to any one of the preceding product clauses, which is any one of the compounds mentioned specifically in the above specification such as in the specific examples, especially any one of the examples 1 et seq. below
48. The use of a compound according to any one of the preceding product clauses for the preparation of a pharmaceutical composition for the treatment of diabetes.
49. The use of a compound according to any one of the preceding product clauses for the preparation of a pharmaceutical composition which can be administered pulmonary for the treatment of diabetes.
50. The use of a compound according to any one of the preceding product clauses for the preparation of a pharmaceutical composition which can be administered pulmonary for the treatment of diabetes and which gives a long acting effect.

51. The use of a compound according to any one of the preceding product clauses for the preparation of a powder pharmaceutical composition which can be administered pulmonary for the treatment of diabetes.

52. The use of a compound according to any one of the preceding product clauses for the preparation of a liquid pharmaceutical composition which can be administered pulmonary for the treatment of diabetes.

53. The use of a compound according to any one of the preceding product clauses for the preparation of a pharmaceutical composition which can be administered orally for the treatment of diabetes.

54. A method of treatment of diabetes, the method comprising administering to a subject in need thereof a therapeutically effective amount of a compound according to any one of the preceding product clauses.

55. A composition containing human insulin as well as a PEGylated insulin analogue according to any one of the preceding clauses.

56. A composition containing insulin aspart as well as a PEGylated insulin analogue according to any one of the preceding clauses.

57. A composition containing insulin Lispro as well as a PEGylated insulin analogue according to any one of the preceding clauses.

58. A composition containing insulin Glulisine as well as a PEGylated insulin analogue according to any one of the preceding clauses.

59. A pharmaceutical composition comprising a biologically active amount of the insulin analogue according to any one of the above clauses relating to insulin analogs and a pharmaceutically acceptable carrier.

60. A method for the treatment, prevention or alleviation of hyperglycemia, type 2 diabetes, impaired glucose tolerance, type 1 diabetes, obesity, syndrome X or dyslipidemia in a subject comprising administering to a subject an insulin analogue according to any one of the above clauses relating to insulin analogs or a pharmaceutical composition according to any one of the above clauses.

61. Use of a therapeutically effective amount of an insulin analogue according to any one of the above clauses relating to insulin analogs for the preparation of a pharmaceutical formulation for the treatment or prevention of hyperglycemia, type 2 diabetes, impaired glucose tolerance, type 1 diabetes, obesity, syndrome X or dyslipidemia.

62. A method of treatment of diabetes, the method comprising administering to a subject in need thereof a therapeutically effective amount of a PEGylated insulin according to any one of the preceding product clauses.

Combining one or more of the clauses described herein, optionally also with one or more of the claims below, results in further clauses and the present invention relates to all possible combinations of said clauses and claims.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

In the following list, selected PEGylation reagents are listed as activated N-hydroxysuccinimide esters (OSu). Obviously, other active esters may be employed, such as 4-nitrophenoxy and many other active esters known to those skilled in the art. The PEG (or mPEG) moiety, $CH_3O-(CH_2CH_2O)_n-$, can be of any size up to Mw 40.000 Da, e.g., 750 Da, 2000 Da, 5000 Da, 20.000 Da and 40.000 Da. The mPEG moiety can be polydisperse but also monodisperse consisting of mPEG's with well defined chain lengths (and, thus, molecular weights) of, e.g., 12 or 24 repeating ethylene glycol units—denoted $mdPEG_x$ for m: methyl/methoxy endcapped, d: discrete and x for the number of repeating ethylene glucol residues, e.g., 12 or 24. The PEG moiety can be either straight chain or branched. The structure/sequence of the PEG-residue on the extended insulin can formally be obtained by replacing the leaving group (e.g., "—OSu") from the various PEGylation reagents with "NH-insulin", where the insulin is PEGylated either in an epsilon position in a lysine residue or in the alpha-amino position in the A- or B-chain (or both), e.g.:

mPEG-COCH$_2$CH$_2$CO—OSu,
mPEG-COCH$_2$CH$_2$CH$_2$CO—OSu,
mPEG-CH$_2$CO—OSu,
mPEG-CH$_2$CH$_2$CO—OSu,
mPEG-CH$_2$CH$_2$CH$_2$CO—OSu,
mPEG-CH$_2$CH$_2$CH$_2$CH$_2$CO—OSu,
mPEG-CH$_2$CH$_2$CH$_2$CH$_2$CH$_2$CO—OSu,
mPEG-CH$_2$CH(CH$_3$)CO—OSu,
mPEG-CH$_2$CH$_2$CH(CH$_3$)CO—OSu,
mPEG-CH$_2$CH$_2$NH—COCH$_2$CH$_2$CO—OSu,
mPEG-CH$_2$CH$_2$CH$_2$NH—COCH$_2$CH$_2$CH$_2$CO—OSu,
mPEG-CH$_2$CH$_2$CH$_2$NH—COCH$_2$CH$_2$CO—OSu,
mPEG-CH$_2$CH$_2$NH—COCH$_2$CH$_2$CH$_2$CO—OSu, mPEG-CO-(4-nitrophenoxy),
(mdPEG$_{12}$-CH$_2$CH$_2$NHCOCH$_2$CH$_2$OCH$_2$)$_3$CNHCOCH$_2$CH$_2$(OCH$_2$CH$_2$)$_4$NHCOCH$_2$CH$_2$CO—OSu (or, in short: (mdPEG$_{12}$)$_3$-dPEG$_4$-OSu),
(mdPEG$_{12}$-CH$_2$CH$_2$NHCOCH$_2$CH$_2$OCH$_2$)$_3$CNHCOCH$_2$CH$_2$(OCH$_2$CH$_2$)$_4$NHCOCH$_2$CH$_2$CO—OSu (or, in short: (mdPEG$_{12}$)$_3$-dPEG$_4$-OSu), mdPEG$_x$-COCH$_2$CH$_2$CO—OSu,
mdPEG$_x$-COCH$_2$CH$_2$CH$_2$CO—OSu,
mdPEG$_x$-CH$_2$CO—OSu,
mdPEG$_x$-CH$_2$CH$_2$CO—OSu,
mdPEG$_x$-CH$_2$CH$_2$CH$_2$CO—OSu,
mdPEG$_x$-CH$_2$CH$_2$CH$_2$CH$_2$CO—OSu,
mdPEG$_x$-CH$_2$CH$_2$CH$_2$CH$_2$CH$_2$CO—OSu,
mdPEG$_x$-CH$_2$CH(CH$_3$)CO—OSu,
mdPEG$_x$-CH$_2$CH$_2$CH(CH$_3$)CO—OSu,
mdPEG$_x$-CH$_2$CH$_2$NH—COCH$_2$CH$_2$CO—OSu,
mdPEG$_x$-CH$_2$CH$_2$CH$_2$NH—COCH$_2$CH$_2$CH$_2$CO—OSu,
mdPEG$_x$-CH$_2$CH$_2$CH$_2$NH—COCH$_2$CH$_2$CO—OSu,
mdPEG$_x$-CH$_2$CH$_2$NH—COCH$_2$CH$_2$CH$_2$CO—OSu or
mdPEG$_x$-CO-(4-nitrophenoxy),
wherein x is an integer in the range from about 6 to about 48, e.g., 12 or 24.

In addition, larger PEGylation reagents can be prepared by assembling two or more smaller PEG reagents. For example, end-capped PEG reagents as N-hydroxysuccinimide esters like any of the ones above can be coupled to (optionally protected) PEG moieties that are functionalised by amino-groups in one end and carboxylic acid (esters) in the other end. After deprotection of the carboxylic acid (if necessary), the carboxylic acid is activated eg. as the N-hydroxysuccinimide ester to furnish a longer PEGylation reagent. If desired, the obtained PEGylation reagent can be further extended by repeating the cycle one or more times. This principle and methodology is illustrated below.

This methodology enables construction of larger monodisperse (and polydisperse) PEGylation reagents of tailored sizes.

Examples of PEG residues of the invention includes:
mPEG750 (where "750" indicates the average molecular weight in Da),
mPEG2000,
mPEG5000,
mPEG10000,
mPEG20000,
mPEG30000,
mPEG40000,
mdPEG$_{12}$, (wherein "12" in subscript indicates the number of PEG monomers—as defined herein and e.g. by Quanta BioDesign Ltd.)
mdPEG$_{24}$,
mdPEG$_{3×12}$ (wherein "3×12" in subscript indicates that PEG is branched and composed of 3 arms each composed of 12 PEG monomers—as defined herein (mdPEG$_{12}$)$_3$-dPEG$_4$-OSu), and, e.g., by Quanta BioDesign Ltd.),
mdPEG$_{4×4}$ (wherein "4×4" in subscript indicates that PEG is branched and composed of 4 arms each composed of 4 PEG monomers—as defined herein (below in "preferred insulins") and, e.g., by IRIS Biotech GMBH),
mdPEG$_{12}$-dPEG$_{12}$ (wherein mdPEG$_{12}$-dPEG$_{12}$ indicates that the PEG residue is assembled from a mdPEG$_{12}$ residue and a amino-dPEG$_{12}$-acid residue as indicated above and illustrated below),
mdPEG$_{12}$-dPEG$_{24}$,
mdPEG$_{24}$-dPEG$_{12}$,
mdPEG$_{24}$-dPEG$_{24}$,
mdPEG$_{24}$-dPEG$_{24}$-dPEG$_{24}$,
mdPEG$_{3×12}$-dPEG$_{12}$,
mdPEG$_{3×12}$-dPEG$_{24}$-dPEG$_{24}$,
mdPEG$_{4×4}$-dPEG$_{12}$ or
mdPEG$_{4×4}$-dPEG$_{24}$.

The PEGylated insulins of this invention have in the following all been named as if the linker connecting the PEG moiety to the insulin in all cases is a (3-)propionyl linker. It is evident from the foregoing that many types of linkers are commercially available and since it is not the exact structure/-composition of the linker that governs the beneficial effects of placing the PEG moiety at residues outside the sequence of regular insulin, it is to be understood that all types of linkers (cf. above) are within the scope of this invention.

Parent protease stabilised insulins of the invention comprise the following A14E, B25H human insulin; A14E, B25H, desB30 human insulin; A14H, B25H, human insulin and A14H, B25H, desB30 human insulin.

EXAMPLES

The following examples are offered by way of illustration, not by limitation.

General Procedure (A) for Preparation of PEGylated, Protease Stabilised Insulins of this Invention The general procedure (A) is illustrated in the first example.

Example 1

General Procedure (A)

A14E, B25H, B29K(N$^\epsilon$-3-mdPEG$_{24}$-Propionyl), desB30 Human Insulin

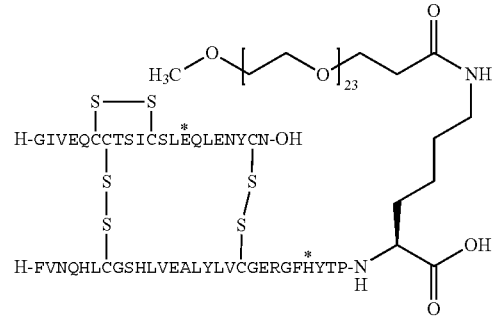

A14E, B25H desB30 human insulin (1.5 g) was dissolved in 0.1 M Na$_2$CO$_3$ (34 ml) and pH was adjusted to 10 with 1N NaOH. mdPEG$_{24}$-SPA (0.45 g, Quanta BioDesign Ltd.) dissolved in MeCN (16.8 ml) was added and the mixture was slowly stirred for 1 hour. Water (25 ml) was added, pH was adjusted to 5.5 with 1N HCl and the mixture was lyophilised. The title compound was obtained by preparative HPLC purification. Column: C18, 3 cm. A-Buffer: 0.1% TFA in MiliQ Water; B-buffer: 0.1% TFA in acetonitrile. Gradient 10-55% B over 45 min. Yield: 650 mg.

MALDI-MS (matrix: HCCA); m/z: 6762, calcd: 6762.

This compound has substantial protracted pulmonary efficacy.

The compound of example 1 (i.e. A14E, B25H, B29K(N$^\epsilon$-3-mdPEG$_{24}$-propionyl), desB30 human insulin) and insulin aspart were tested by rat intratracheal drop instillation by the procedure described in example 10 below. The number of animals in each group was 4-5. The doses given of the compound of example 1 were 10, 20 and 40 nmol/kg intratracheally and the blood glucose levels (mM) obtained as a function of time (minutes) are given in FIG. 1 below. The doses given of insulin aspart were 5, 10 and 15 nmol/kg intratracheally and the blood glucose levels (mM) obtained as a function of time (minutes) are given in FIG. 1 below. As appears from FIG. 1, the compound of this invention has a dose dependent blood glucose lowering effect that is protracted following pulmonary dosing.

Example 2

General Procedure (A)

A14E, B25H, B29K(N$^\epsilon$-3-mPEG2.000-Propionyl), desB30 Human Insulin

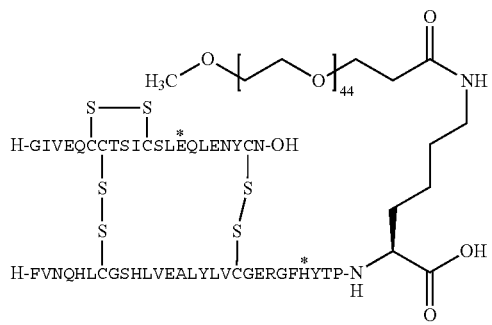

MALDI-MS (matrix: sinapinic acid); m/z: 7850 (broad).

Example 3

General Procedure (A)

A14E, B25H, B29K(N$^\epsilon$3-{mPEG750}Propionylcarbamoyl), desB30 Human Insulin

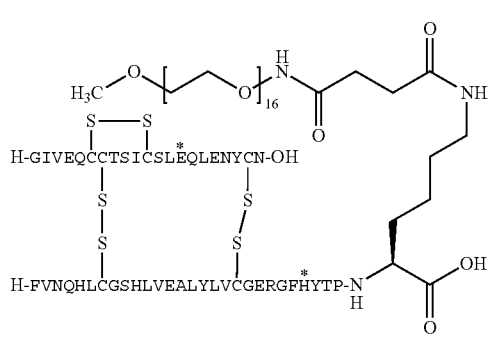

MALDI-MS (matrix: sinapinic acid); m/z: 6570 (broad).

Example 4

General Procedure (A)

A14E, B25H, B29K(N$^\epsilon$-3-{2-[2-(2-Methoxyethoxy)ethoxy]ethoxy}propionyl), desB30 Human Insulin

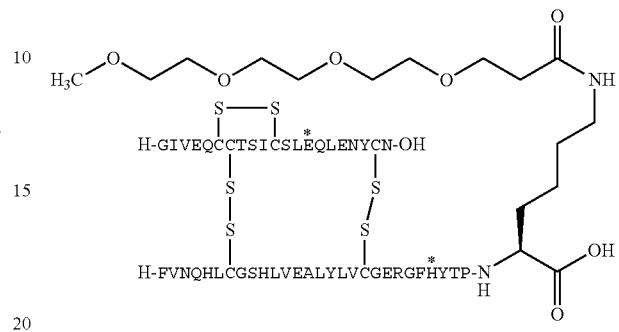

tert-Butyl 3-{2-[2-(2-methoxyethoxy)ethoxy]ethoxy}propionate

Triethylene glycol monomethyl ether (1.0 g, 6.1 mmol) and tert-butyl acrylate (390 mg, 3.05 mmol) were dissolved in dry THF and sodium metal (0.7 mg, 0.03 mmol) was added at room temperature. The mixture was stirred for 4 hours and 1 M HCl was added to quench the reaction. The mixture was extracted twice with dichloromethane, and the organic phase was dried over MgSO$_4$ and concentrated in vacuo to provide an oil, which was purified by silica chromatography using ethyl acetate as eluent. The product was an oil, 773 mg (44%).
LCMS m=237.1 (M-tBu)

Succinimidyl 3-{2-[2-(2-methoxyethoxy)ethoxy]ethoxy}propionate tert-Butyl 3-{2-[2-(2-Methoxyethoxy)ethoxy]ethoxy}propionate (131 mg, 0.45 mmol) was dissolved in trifluoroacetic acid and left at room temperature for 1 hour. The solvent was removed in vacuo and residual trifluoroacetic acid was removed by evaporation from dioxane. The deprotected intermediate was dissolved in dichloromethane and treated with N-hydroxysuccinimide (57 mg, 0.49 mmol) and ethyl-3-(3-dimethylaminopropyl)carbodiimide hydrochloride (86 mg, 0.45 mmol) and stirred at room temperature overnight. The reaction mixture was diluted with dichloromethane and washed twice with water. The organic phase was dried over MgSO$_4$ and concentrated in vacuo to provide 122 mg (82%).

Figure 2:
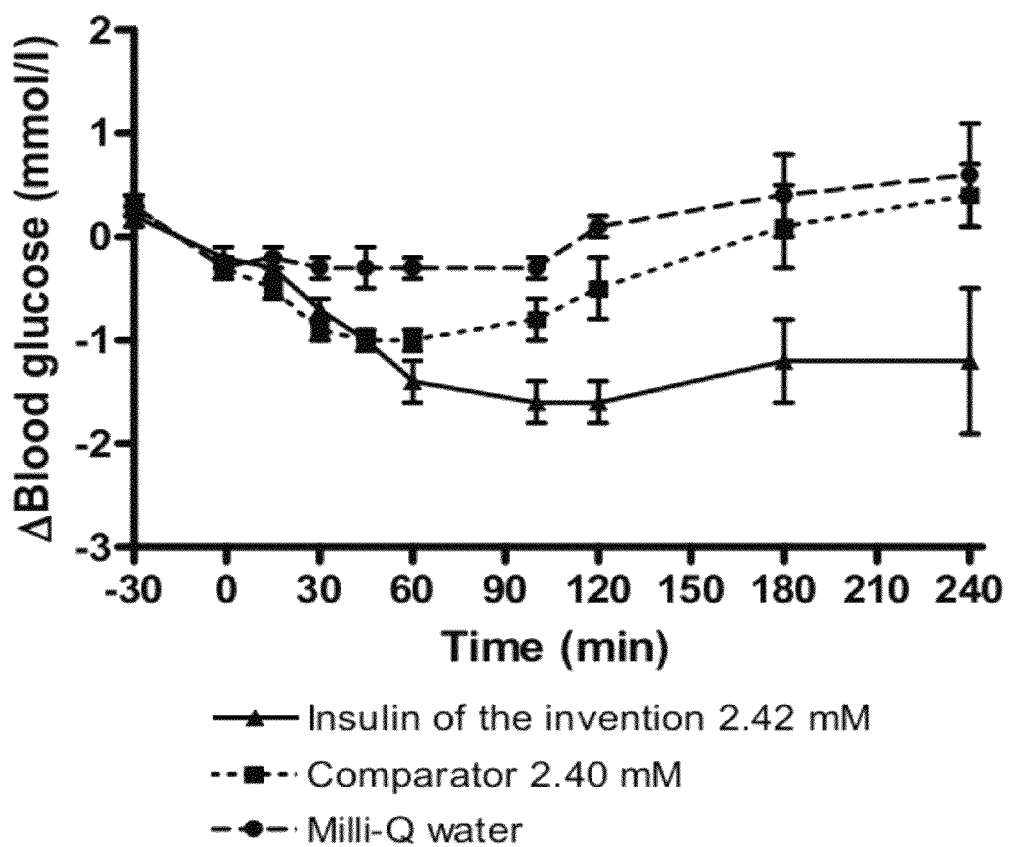
FIG. 2 is the blood glucose profile of the insulin of example 4 compared with a comparator (B29K(N$^\epsilon$-3-{2-[2-(2-methoxyethoxy)ethoxy]ethoxy}propionyl), desB30 human insulin) following injection into mid-jejunum of rats. The protocol is described in example 11. There were used 7 animals per treatment group and 3 animals in the vehicle group. Dose volumes given: 0.4 ml/kg.

A14E, B25H, B29K(N$^\epsilon$-3-{2-[2-(2-Methoxyethoxy)ethoxy]ethoxy}propionyl) desB30 Human Insulin A14E, B25H desB30 Insulin (500 mg, 0.08 mmol) was dissolved in 0.1 M sodium carbonate (6 mL) at room temperature, pH 10.5. Succinimidyl 3-{2-[2-(2-methoxyethoxy)ethoxy]ethoxy}propionate (35 mg, 0.11 mmol) was dissolved in acetonitrile and added to the insulin solution. pH was now 10.3. After 30 min, the reaction mixture was quenched with 0.1 M methylamine (0.6 mL). The insulin product was purified by RP-HPLC on C4 column, A-buffer 0.1% trifluoroacetic acid in water, B-buffer 0.1% TFA in acetonitrile, to provide 227 mg (44%).
ES-MS; m/z: 5879.6. (deconvoluted)
The compound of example 4 (i.e., A14E, B25H, B29K(N$^\epsilon$-3-{2-[2-(2-methoxyethoxy)ethoxy]ethoxy}-propionyl), desB30 human insulin) was compared with B29K(N$^\epsilon$-3-{2-[2-(2-methoxyethoxy)ethoxy]-ethoxy}propionyl), desB30 human insulin (designated "Comparator" in FIG. 2 below) in a rat ileum injection of the insulins using the method described in example 11 below. The insulin of example 4 and the comparator were applied into mid-jejunum of fasted SPRD rats (mean±SEM; dose volume given: 0.4 ml/kg). The animal group sizes were: Insulin of the invention & Comparator, n=7, and vehicle (Milli-Q water), n=3. The results obtained (decrease in blood glucose (mmol/1) depending on time (in minutes)) are given in FIG. 2 below. As appears from FIG. 2, the compound of this invention (i.e., A14E, B25H, B29K(N$^\epsilon$-3-{2-[2-(2-methoxyethoxy)ethoxy]ethoxy}propionyl), desB30 human insulin) has a pronounced improved potency and prolonged action, compared with B29K(N$^\epsilon$-3-{2-[2-(2-methoxyethoxy)ethoxy]ethoxy}propionyl), desB30 human insulin after application into mid-jejunum of fasted SPRD rats (as a model of oral delivery). Hence, after less than 3 hours, there is no measurable effect from B29K(N$^\epsilon$-3-{2-[2-(2-methoxyethoxy)ethoxy]ethoxy}propionyl), desB30 human insulin whereas after 4 hours the suppression of blood glucose is still maximal for the compound of this invention.

Example 5

General Procedure (A)

B25H, B29K(N$^\epsilon$-3-(mdPEG$_{12}$)Propionyl) Human Insulin

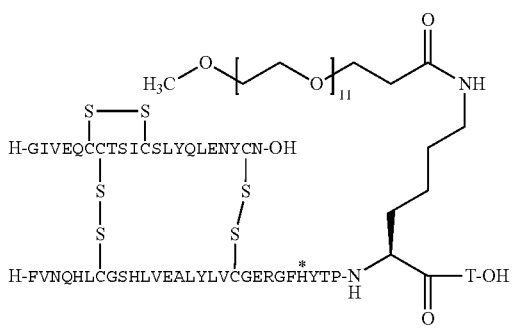

MALDI-MS (matrix: sinapinic acid); m/z: 6365.

Example 6

Insulin Receptor Binding of the Insulin Derivatives of this Invention

The affinity of the insulin derivatives of this invention for the human insulin receptor is determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the GraphPad Prism 2.01 (GraphPad Software, San Diego, Calif.).

Insulin Receptor Binding Affinities of Selected Compounds of this Invention:
Ex. No: Insulin receptor binding,
    A-isoform (without exon 11):
    (Relative to human insulin)
1 2.2%
2 1.4%
3 3.4%
4 17%
5 10%

Example 7

Comparison of Proteolytic Stability (Half-Life) of Insulin Analogues and Human Insulin Towards Chymotrypsin Proteolytic stability of human insulin and insulin analogues (0.6 mM, 10 µL) towards chymotrypsin (0.34 or 3.4 µg, 3.4 µL of 0.1 or 1 µg/µL) was measured after incubation in 100 mM NH$_4$HCO$_3$ pH8.1 or 5 mM NaP, 140 mM NaCl, 70 ppm Tween20, pH 7.4 and 37° C. at a final volume of 100 µL. At various times (0, 5, 15, 30, 60 min) samples were quenched with an equal volume of 0.2% TFA and transferred to 5° C. Human insulin and insulin analogues were immediately analyzed by RP-HPLC at 214 nm and the area under the peak corresponding to intact protein was determined. Half-lives (T$_{1/2}$) were obtained from the curves and the fold increase/decrease compared to human insulin was calculated (Stability relative fold).

Relative Stability Towards Chymotrypsin Digestion of Selected Compounds of this Invention:
Ex. No: Stability towards chymotrypsin
    digestion:
    (Fold relative to human insulin)
1 14x
2 16x
4 11x Example 8

Blood Glucose Lowering Effect after i.v. Bolus Injection in Rat of the Insulin Derivatives of this Invention Male Wistar rats, 200-300 g, fasted for 18 h, is anesthetized using either Hypnorm-Dormicum s.c. (1.25 mg/ml Dormicum, 2.5 mg/ml fluanisone, 0.079 mg/ml fentanyl citrate) 2 ml/kg as a priming dose (to timepoint −30 min prior to test substance dosing) and additional 1 ml/kg every 20 minutes.

The animals are dosed with an intravenous injection (tail vein), 1 ml/kg, of control and test compounds (usual dose range 0.125-20 nmol/kg). Blood samples for the determination of whole blood glucose concentration are collected in heparinized 10 µl glass tubes by puncture of the capillary vessels in the tail tip to time −20 min and 0 min (before dosing), and to time 10, 20, 30, 40, 60, 80, 120, and 180 min after dosing. Blood glucose concentrations are measured after dilution in analysis buffer by the immobilized glucose oxidase method using an EBIO Plus autoanalyzer (Eppendorf, Germany). Mean plasma glucose concentrations courses (mean±SEM) are made for each dose and each compound.

Example 9

Potency of the Insulin Derivatives of this Invention Relative to Human Insulin

Sprague Dawley male rats weighing 238-383 g on the experimental day are used for the clamp experiment. The rats have free access to feed under controlled ambient conditions and are fasted overnight (from 3 pm) prior to the clamp experiment.

Experimental Protocol:

The rats are acclimatized in the animal facilities for at least 1 week prior to the surgical procedure. Approximately 1 week prior to the clamp experiment, Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

At 7 am on the experimental day overnight fasted (from 3 pm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and have free access to drinking water. After a 30 min basal period during which plasma glucose levels were measured at 10 min intervals, the insulin derivative to be tested and human insulin (one dose level per rat, n=6-7 per dose level) are infused (i.v.) at a constant rate for 300 min. Plasma glucose levels are measured at 10 min intervals throughout and infusion of 20% aqueous glucose is adjusted accordingly in order to maintain euglyceamia. Samples of re-suspended erythrocytes are pooled from each rat and returned in about ½ ml volumes via the carotid catheter.

On each experimental day, samples of the solutions of the individual insulin derivatives to be tested and the human insulin solution are taken before and at the end of the clamp experiments and the concentrations of the peptides are confirmed by HPLC. Plasma concentrations of rat insulin and C-peptide as well as of the insulin derivative to be tested and human insulin are measured at relevant time points before and at the end of the studies. Rats are killed at the end of experiment using a pentobarbital overdose.

Example 10

Pulmonary Delivery of Insulin Derivatives to Rats

The test substance will be dosed pulmonary by the drop instillation method. In brief, male Wistar rats (app.250 g) are anaesthesized in app. 60 ml fentanyl/dehydrodenzperidol/-dormicum given as a 6.6 ml/kg sc primingdose and followed by 3 maintainance doses of 3.3 ml/kg sc with an interval of 30 min given at time points −10, 20, 50 and 95 min. Ten minutes after the induction of anaesthesia, basal samples are obtained from the tail vein (t=−20 min) followed by a basal sample immediately prior to the dosing of test substance (t=0). At t=0, the test substance is dosed intra tracheally into one lung. A special cannula with rounded ending is mounted on a syringe containing the 200 μl air and test substance (1 ml/kg). Via the orifice, the cannula is introduced into the trachea and is forwarded into one of the main bronchi—just passing the bifurcature. During the insertion, the neck is palpated from the exterior to assure intratracheal positioning. The content of the syringe is injected followed by 2 sec pause. Thereafter, the cannula is slowly drawn back. The rats are kept anaesthesized during the test (blood samples for up to 4 or 8 hrs) and are euthanized after the experiment.

Example 11

Blood Glucose Lowering Effect of Insulin Analogues of the Invention Injected into Ileum of Sprague-Dawley Rats Male Sprague-Dawley (SPRD) rats, 250-350 g, fasted for 18 h are anesthetized using Hypnorm-Dormicum s.c. (0.079 mg/ml fentanyl citrate, 2.5 mg/ml fluanisone and 1.25 mg/ml midazolam) 2 ml/kg as a priming dose (to time point −60 min prior to test substance dosing), 1 ml/kg after 20 min followed by 1 ml/kg every 40 min.

The anesthetized rats are placed on a homeothermic blanket stabilized at 37° C. A 20 cm polyethylene catheter is filled with insulin solution and inserted into the ileum 3-4 cm from the caecum. The catheter tip is placed approx. 2 cm inside the lumen of the target-segment. At time 0, the rats are dosed via the catheter, 0.4 ml/kg of test or control compounds (usual dose range 240-1440 nmol/kg). Blood samples for the determination of whole blood glucose concentrations are collected in heparinised 10 μl capillary tubes by puncture of the capillary vessels in the tail tip to time −30 and 0 min (before dosing) and to time 10, 20, 30, 60, 100, 120, 180 and 240 min. Blood glucose concentrations are measured after dilution in analysis buffer by the glucose oxidase method using an EBIO Plus autoanalyzer (Eppendorf, Germany). Mean blood glucose concentration courses (mean±SEM) are made for each compound.

Other preferred protease stabilised PEGylated insulins of the invention may be prepared similarly and as described below Example 12

Preferred protease stabilised PEGylated insulins of the invention that may be prepared similarly as the protease stabilised PEGylated insulins described above in the examples includes A14E, B25H, B29K(N$^\epsilon$mdPEG$_{12}$-dPEG$_{24}$-propionyl), desB30 human insulin

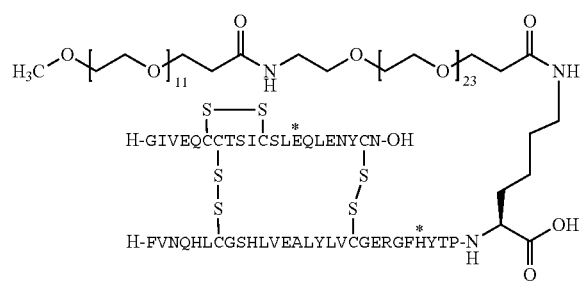

The PEGylation reagent can be prepared as described in the following:

Preparation of omega-(methoxy-PEG$_{11}$-propanoylamino)-PEG$_{24}$-propanoic acid (mdPEG$_{12}$-dPEG$_{24}$ acid)

Omega-(methoxy-PEG$_{11}$-propanoylamino)PEG$_{24}$-propanoic acid (249 mg, 0.145 mmol) was dissolved in acetonitrile (10 mL) and pH was adjusted to 8 by addition of DIPEA (measurement of pH was done using wet indicator strips). TSTU (48 mg, 0.16 mmol) in acetonitrile (10 mL) was added and the mixture was stirred at room temperature for 1.5 h, and

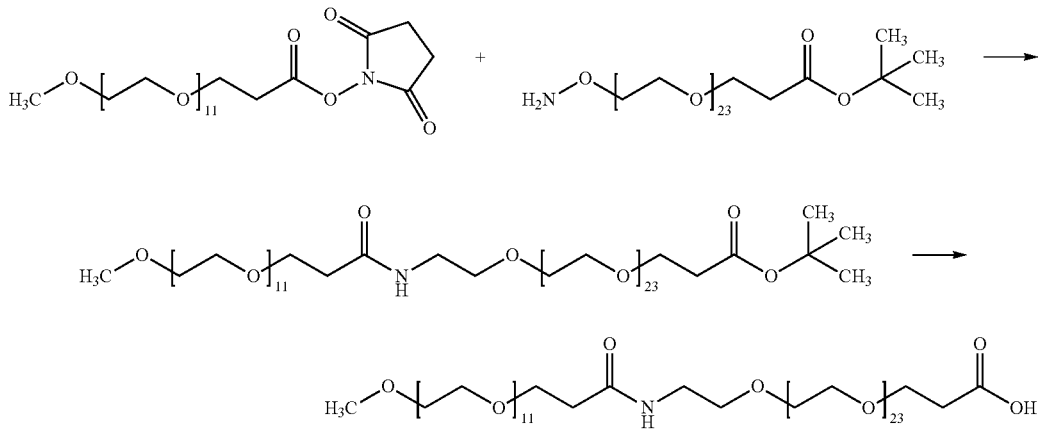

mdPEG$_{12}$ NHS ester (0.457 mmol, Quanta BioDesign Ltd. Product No 10262) and amino-dPEG$_{24}$ tert-butylester (0.416 mmol, Quanta BioDesign, Product No 10311) were dissolved separately in acetonitrile (each 10 mL) and then the two solutions were mixed, pH was adjusted with DIPEA to pH 8 (measurement of pH was done using wet indicator strips). The resulting mixture was stirred at RT overnight, and subsequently evaporated to dryness, followed by treatment with TFA/DCM (1/1), 10 mL for 1 h at RT. The mixture was then evaporated to dryness and stripped twice with DCM. The residue was purified by HPLC (2 cm, C18 column) using acetonitrile (AcCN)/0.1% TFA and water/0.1% TFA as eluents. Gradient: 10-80% AcCN/TFA from 5-20 min. Fractions containing the desired compound were collected, combined and evaporated to dryness resulting in omega-(methoxy-PEG$_{11}$-propanoyl-amino)PEG$_{23}$-propanoic acid as an oil (249 mg, 35%).

LCMS: m/z: 1718 (M+1)$^+$.

Preparation of omega-(methoxy-PEG$_{11}$-propanoylamino)-PEG$_{24}$-propanoic acid N-hydroxysuccinimide ester (mdPEG$_{12}$-dPEG$_{24}$-NHS or mdPEG$_{12}$-dPEG$_{24}$-propanoic acid OSu ester)

evaporated to dryness. The residue was dissolved in DCM and washed with hydrochloric acid (0.01 M), the organic phase was dried (MgSO$_4$), filtered and the filtrate was evaporated to dryness. The resulting omega-(methoxy-PEG$_{11}$-propanoylamino)PEG$_{24}$ propanoic acid N-hydroxysuccinimide ester was used for coupling to insulin without further purification.

LCMS: m/z 1813.8 (M+1)$^+$.

Examples 13-19

Similarly, other PEGylation reagents for the following preferred insulins may be prepared similarly.

A14E, B25H, B29K(N$^\epsilon$(mdPEG$_{24}$-yl-dPEG$_{24}$-yl), desB30 Human Insulin:

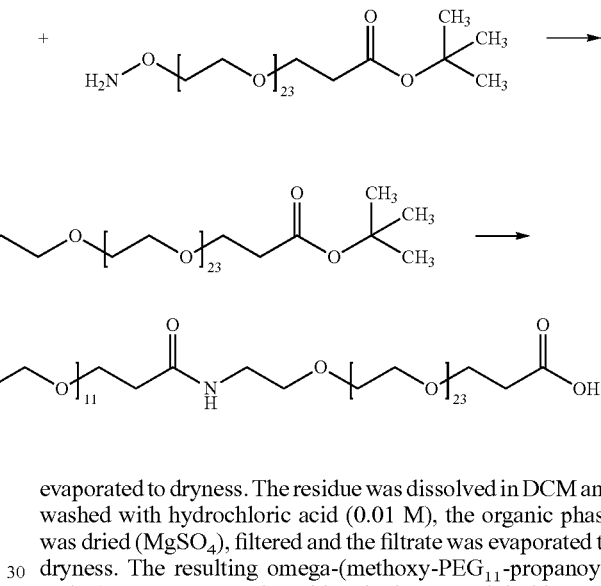

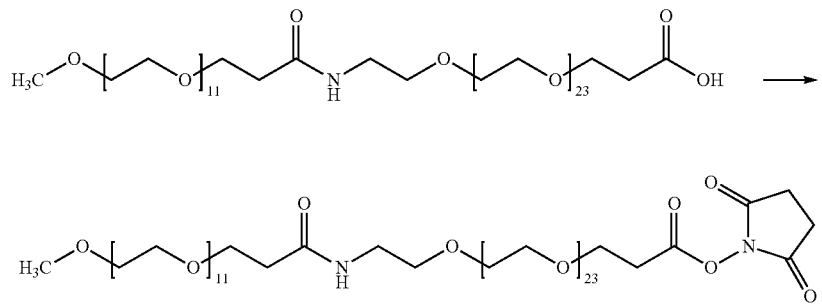

A14E, B25H, B29K(N^ε(mdPEG_{12})_3-dPEG_4-yl), desB30 Human Insulin:
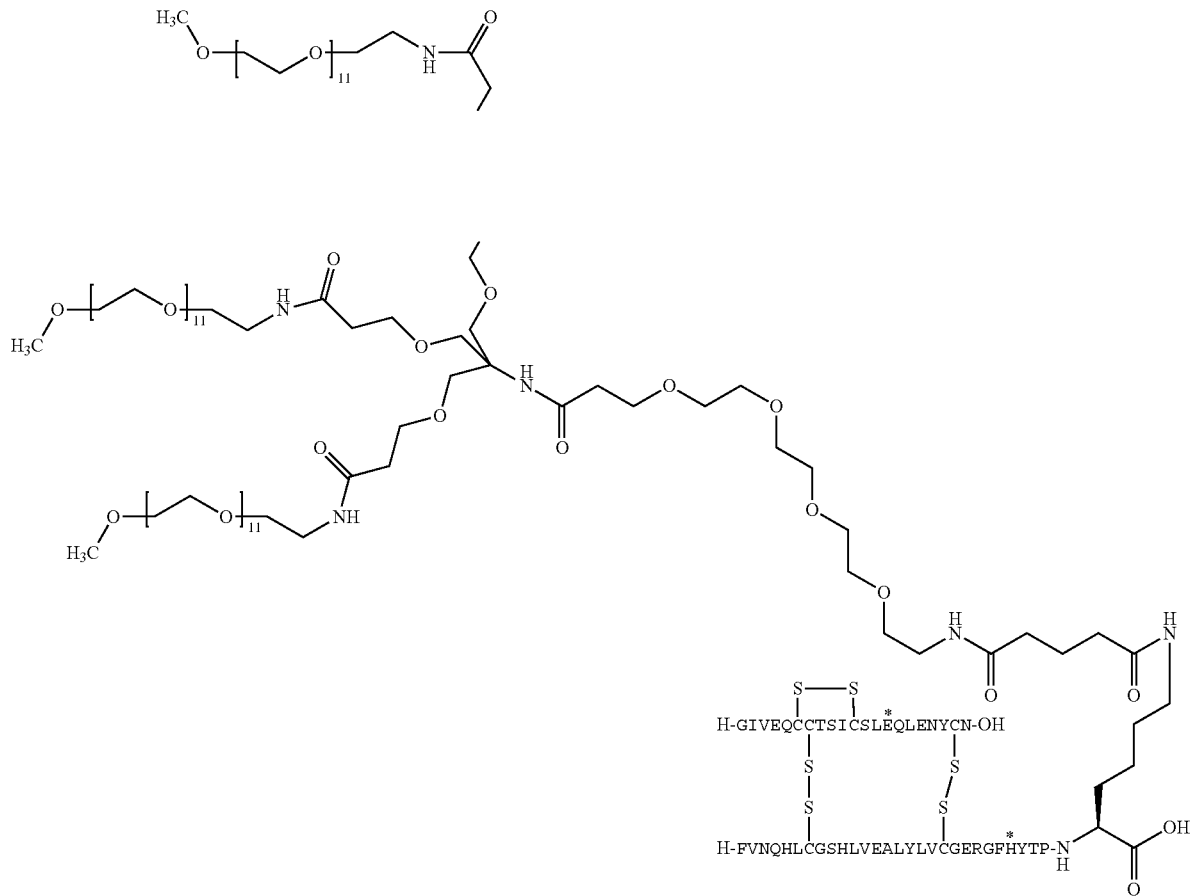
A14E, B25H, B29K(N^ε(mdPEG_{12})_3-dPEG_4-yl-dPEG_{12}-yl), desB30 Human Insulin:
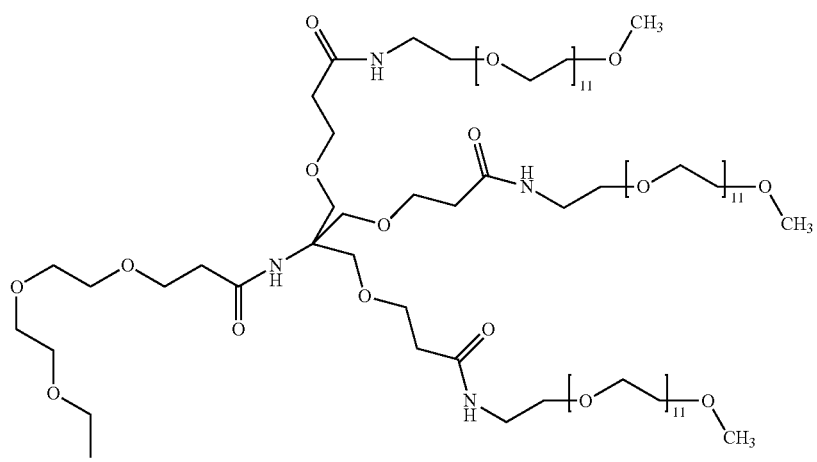

-continued
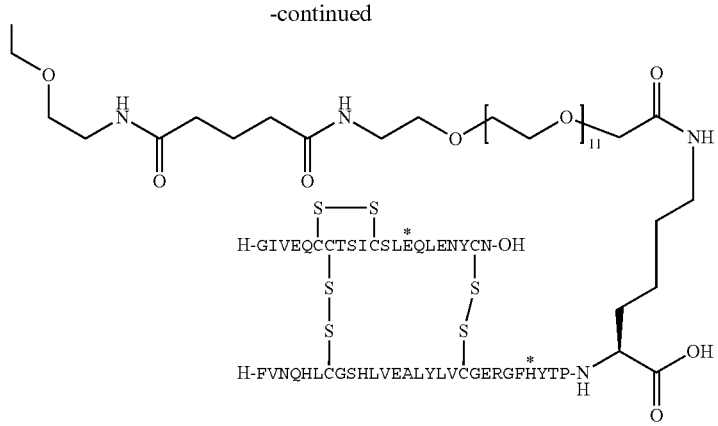
A14E, B25H, B29K(N$^\epsilon$(mdPEG$_{12}$)$_3$-dPEG$_4$-yl-dPEG$_{24}$-yl), desB30 Human Insulin:
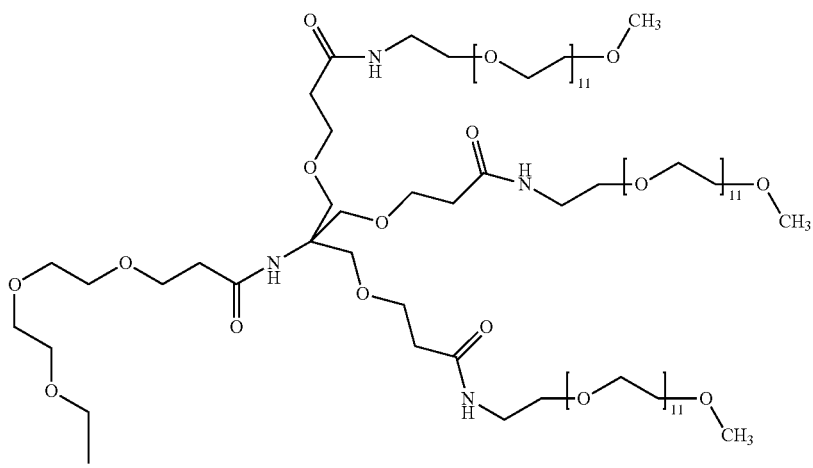
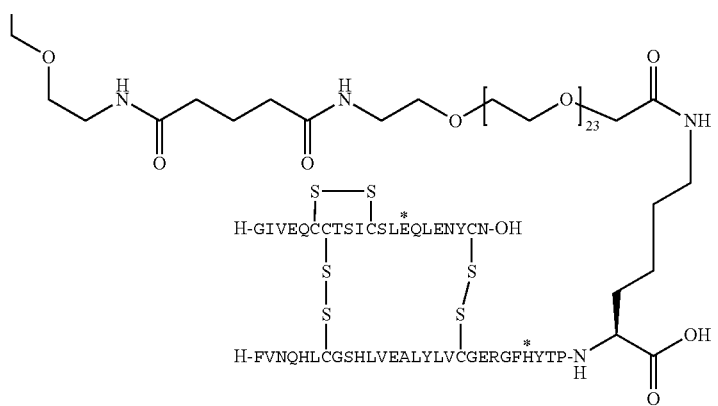

A14E, B25H, B29K(N$^\epsilon$-3-mdPEG$_{4\times4}$-Propionyl), desB30 Human Insulin:
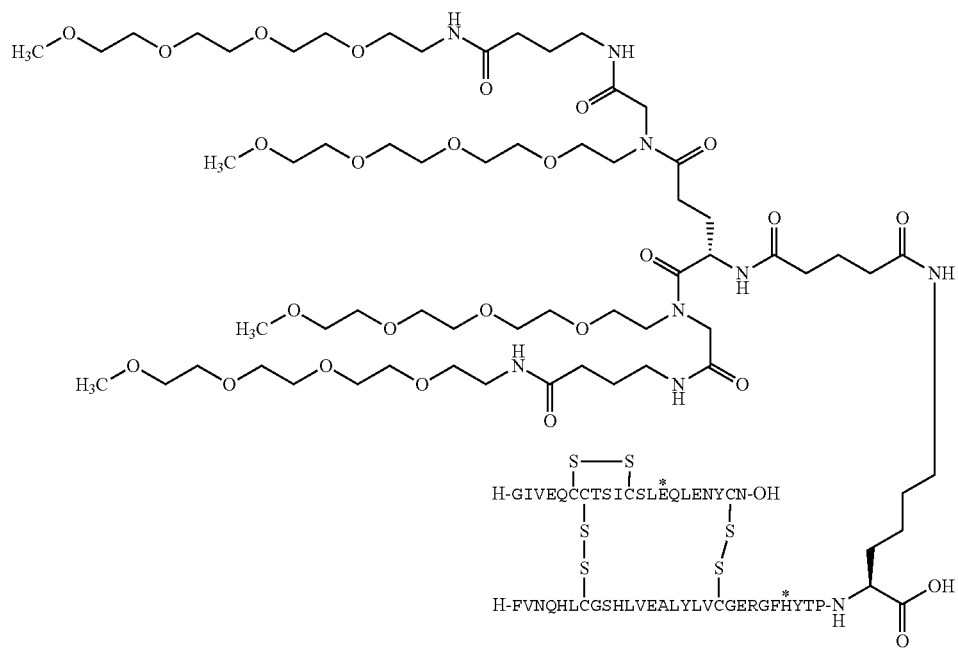
A14E, B25H, B29K(N$^\epsilon$-3-mdPEG$_{4\times4}$-dPEG$_{12}$-Propionyl), desB30 Human Insulin:
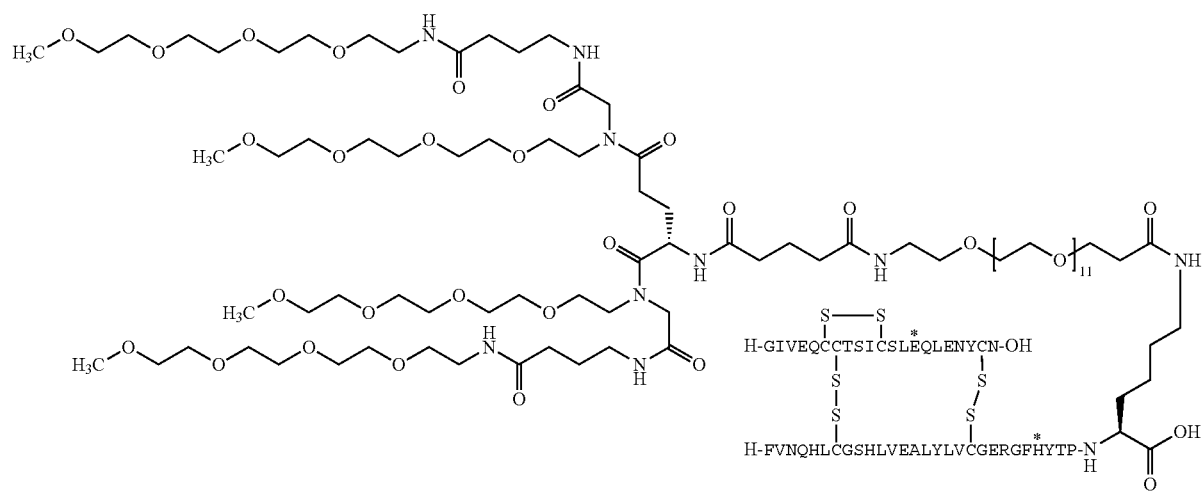

A14E, B25H, B29K(N$^\epsilon$-3-mdPEG$_{4\times4}$-dPEG$_{24}$-Propionyl), desB30 Human Insulin:

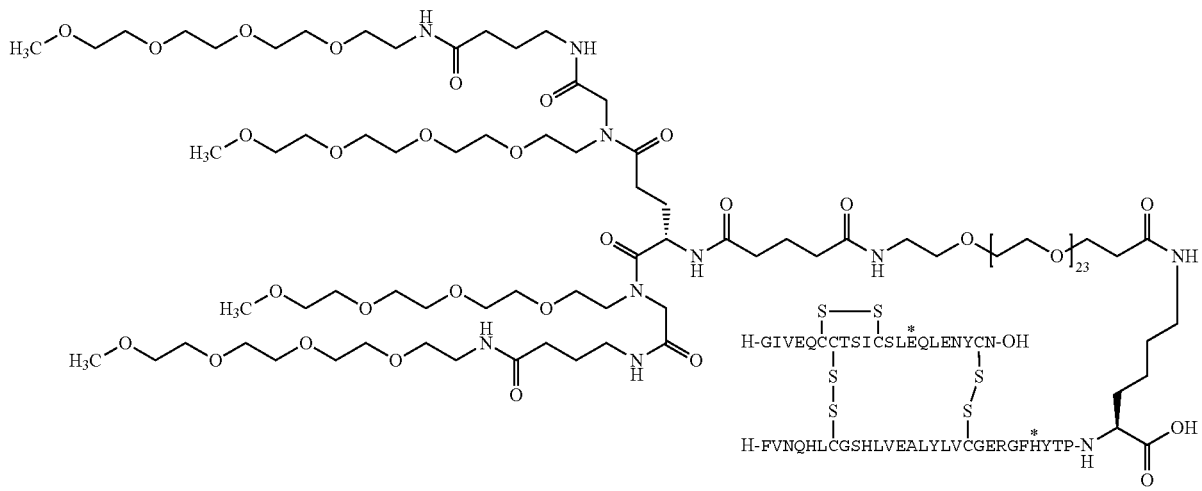

SEQUENCE LISTINGS

SEQ ID NO: 5 is the A chain dealt with in examples 1-4 & 12-19. SEQ ID NO: 6 is the B1-B28 chain dealt with in examples 1-5 & 12-19. SEQ ID NO: 7 is the A chain dealt with in example 5.

What is claimed is:

1. A PEGylated analogue of human insulin, wherein the amino acid in position A14 is Glu (A14E), the amino acid in position B25 is H is (B25H), comprising the desB30 mutation, and wherein the PEG moiety comprises the moiety —(OCH$_2$CH$_2$)$_n$—, wherein n is an integer in the range from 2 to about 500, that via a linker is attached to the ε amino acid in the lysine residue in position B29 (B29K), wherein said linker is a —CO— group, or is derived from an acetic acid moiety with the linking motif —CH$_2$CO—, or a propionic acid with the linking motif —CH$_2$CH$_2$CO— or —CHCH$_3$CO—, or from a butyric acid moiety with the linking motif —CH$_2$CH$_2$CH$_2$CO— or —CH$_2$CHCH$_3$CO—; and
wherein the PEGylated analogue of human insulin has improved stability towards proteolytic degradation at protease cleavage sites.

2. A PEGylated analogue of human insulin, according to claim 1, comprising the moiety —(OCH$_2$CH$_2$)$_n$—, wherein n is an integer in the range from 2 to about 250, from 2 to about 125, from 2 to about 50, from 2 to about 25, or from 2 to about 12.

3. A PEGylated analogue of human insulin, according to claim 1, wherein the polyethylene glycol moiety has a nominal molecular weight in the range from about 200 to about 20,000, from about 200 to about 10,000, from about 200 to about 5,000, from about 200 to about 2,000, from about 200 to about 1,000, or from about 200 to about 750.

4. A PEGylated analogue of human insulin, according to claim 1, wherein the polyethylene glycol moiety is monodisperse.

5. A PEGylated analogue of human insulin, according to claim 1, which is A14E, B25H, B29K(N$^\epsilon$-3-mdPEG$_{24}$-propionyl), desB30 human insulin;
A14E, B25H, B29K(N$^\epsilon$-3-mPEG2.000-propionyl), desB30 human insulin;
A14E, B25H, B29K(N$^\epsilon$3-{mPEG750}-propionylcarbamoyl), desB30 human insulin;
A14E, B25H, B29K(N$^\epsilon$-3-{2-[2-(2-methoxyethoxy)ethoxy]ethoxy}propionyl), desB30 human insulin;
A14E, B25H, B29K(N$^\epsilon$mdPEG$_{12}$-dPEG$_{24}$-propionyl), desB30 human insulin;
A14E, B25H, B29K(N$^\epsilon$(mdPEG$_{24}$-yl-dPEG$_{24}$-yl), desB30 human insulin;
A14E, B25H, B29K(N$^\epsilon$(mdPEG$_{12}$)-3-dPEG$_4$-yl), desB30 human insulin;
A14E, B25H, B29K(N$^\epsilon$(mdPEG$_{12}$)-3-dPEG$_4$-yl-dPEG$_{12}$-yl), desB30 human insulin;
A14E, B25H, B29K(N$^\epsilon$(mdPEG$_{12}$)-3-dPEG$_4$-yl-dPEG$_{24}$-yl), desB30 human insulin;
A14E, B25H, B29K(N$^\epsilon$-3-mdPEG$_{4\times4}$-propionyl), desB30 human insulin;
A14E, B25H, B29K(N$^\epsilon$-3-mdPEG$_{4\times4}$-dPEG$_{12}$-propionyl), desB30 human insulin or
A14E, B25H, B29K(N$^\epsilon$-3-mdPEG$_{4\times4}$-dPEG$_{24}$-propionyl), desB30 human insulin.

6. A pharmaceutical composition comprising a PEGylated analogue of human insulin according to claim 1 and one or more pharmaceutically acceptable carriers or diluents.

7. A pharmaceutical composition according to claim 6, wherein the pharmaceutical composition is formulated in an oral dosage form.

8. A pharmaceutical composition according to claim 6, wherein the pharmaceutical composition is formulated in a pulmonary dosage form.

9. A method for the treatment, prevention or alleviation of hyperglycemia, type 2 diabetes, impaired glucose tolerance, type 1 diabetes, obesity, syndrome X or dyslipidemia in a subject comprising administering to a subject in need thereof an analogue of human insulin according to claim 1 or a pharmaceutical composition thereof.

10. A method for the treatment of diabetes comprising administering to a subject in need thereof, a pharmaceutically effective amount of an analogue of human insulin according to claim 1, or a pharmaceutical composition thereof.

* * * * *

UNITED STATES PATENT AND TRADEMARK OFFICE
CERTIFICATE OF CORRECTION

PATENT NO.      : 8,987,197 B2                                                   Page 1 of 1
APPLICATION NO. : 13/306411
DATED           : March 24, 2015
INVENTOR(S)     : Peter Madsen et al.

It is certified that error appears in the above-identified patent and that said Letters Patent is hereby corrected as shown below:

In the Claims:

Please replace claim 5, column 58, line 37 with the following:

A14E, B25H, B29K(N$^\epsilon$(mdPEG$_{12}$)$_3$-dPEG$_4$-yl), desB30 human insulin;

Please replace claim 5, column 58, line 39 with the following:

A14E, B25H, B29K(N$^\epsilon$(mdPEG$_{12}$)$_3$-dPEG$_4$-yl-dPEG$_{12}$-yl), desB30 human insulin;

Please replace claim 5, column 58, line 41 with the following:

A14E, B25H, B29K(N$^\epsilon$(mdPEG$_{12}$)$_3$-dPEG$_4$-yl-dPEG$_{24}$-yl), desB30 human insulin;

Signed and Sealed this
Twenty-first Day of July, 2015

Michelle K. Lee
*Director of the United States Patent and Trademark Office*

```
                         SEQUENCE LISTING

<160> NUMBER OF SEQ ID NOS: 7

<210> SEQ ID NO 1
<211> LENGTH: 25
<212> TYPE: PRT
<213> ORGANISM: Artificial
<220> FEATURE:
<223> OTHER INFORMATION: Modified Insulin A chain
<220> FEATURE:
<221> NAME/KEY: MISC_FEATURE
<222> LOCATION: (1)..(1)
<223> OTHER INFORMATION: Xaa is absent or Gly
<220> FEATURE:
<221> NAME/KEY: MISC_FEATURE
<222> LOCATION: (2)..(2)
<223> OTHER INFORMATION: Xaa is absent or Pro
<220> FEATURE:
<221> NAME/KEY: MISC_FEATURE
<222> LOCATION: (3)..(3)
<223> OTHER INFORMATION: Xaa is absent or Pro
<220> FEATURE:
<221> NAME/KEY: MISC_FEATURE
<222> LOCATION: (11)..(11)
<223> OTHER INFORMATION: Xaa is Thr or His
<220> FEATURE:
<221> NAME/KEY: MISC_FEATURE
<222> LOCATION: (15)..(15)
<223> OTHER INFORMATION: Xaa is Ser, Asp or Glu
<220> FEATURE:
<221> NAME/KEY: MISC_FEATURE
<222> LOCATION: (16)..(16)
<223> OTHER INFORMATION: Xaa is Leu, Thr, Asn, Asp, Gln, His, Lys, Gly,
      Arg, Pro, Ser or Glu
<220> FEATURE:
<221> NAME/KEY: MISC_FEATURE
<222> LOCATION: (17)..(17)
<223> OTHER INFORMATION: Xaa is Tyr, Thr, Asn, Asp, Gln, His, Lys, Gly,
      Arg, Pro, Ser or Glu
<220> FEATURE:
<221> NAME/KEY: MISC_FEATURE
```

```
<222> LOCATION: (18)..(18)
<223> OTHER INFORMATION: Xaa is Gln, Asp or Glu
<220> FEATURE:
<221> NAME/KEY: MISC_FEATURE
<222> LOCATION: (21)..(21)
<223> OTHER INFORMATION: Xaa is Asn, Lys or Gln
<220> FEATURE:
<221> NAME/KEY: MISC_FEATURE
<222> LOCATION: (24)..(24)
<223> OTHER INFORMATION: Xaa is Asn or Gln
<220> FEATURE:
<221> NAME/KEY: MISC_FEATURE
<222> LOCATION: (25)..(25)
<223> OTHER INFORMATION: Xaa is absent or Lys

<400> SEQUENCE: 1

Xaa Xaa Xaa Gly Ile Val Glu Gln Cys Cys Xaa Ser Ile Cys Xaa Xaa
1               5                   10                  15

Xaa Xaa Leu Glu Xaa Tyr Cys Xaa Xaa
            20              25

<210> SEQ ID NO 2
<211> LENGTH: 35
<212> TYPE: PRT
<213> ORGANISM: Artificial
<220> FEATURE:
<223> OTHER INFORMATION: Modified Insulin B chain
<220> FEATURE:
<221> NAME/KEY: MISC_FEATURE
<222> LOCATION: (1)..(1)
<223> OTHER INFORMATION: Xaa is absent or Gly
<220> FEATURE:
<221> NAME/KEY: MISC_FEATURE
<222> LOCATION: (2)..(2)
<223> OTHER INFORMATION: Xaa is absent or Pro
<220> FEATURE:
<221> NAME/KEY: MISC_FEATURE
<222> LOCATION: (3)..(3)
<223> OTHER INFORMATION: Xaa is absent or Pro
<220> FEATURE:
<221> NAME/KEY: MISC_FEATURE
<222> LOCATION: (4)..(4)
<223> OTHER INFORMATION: Xaa is absent Phe or Glu
<220> FEATURE:
<221> NAME/KEY: MISC_FEATURE
<222> LOCATION: (5)..(5)
<223> OTHER INFORMATION: Xaa is absent or Val
<220> FEATURE:
<221> NAME/KEY: MISC_FEATURE
<222> LOCATION: (6)..(6)
<223> OTHER INFORMATION: Xaa is absent, Asn or Gln
<220> FEATURE:
<221> NAME/KEY: MISC_FEATURE
<222> LOCATION: (7)..(7)
<223> OTHER INFORMATION: Xaa is Gln or Glu
<220> FEATURE:
<221> NAME/KEY: MISC_FEATURE
<222> LOCATION: (13)..(13)
<223> OTHER INFORMATION: Xaa is His, Asp, Pro or Glu
<220> FEATURE:
<221> NAME/KEY: MISC_FEATURE
<222> LOCATION: (19)..(19)
<223> OTHER INFORMATION: Xaa is Tyr, Asp, Gln, His, Arg or Glu
<220> FEATURE:
<221> NAME/KEY: MISC_FEATURE
<222> LOCATION: (27)..(27)
<223> OTHER INFORMATION: Xaa is Phe or His
<220> FEATURE:
<221> NAME/KEY: MISC_FEATURE
<222> LOCATION: (28)..(28)
<223> OTHER INFORMATION: Xaa is Phe or His
<220> FEATURE:
<221> NAME/KEY: MISC_FEATURE
<222> LOCATION: (29)..(29)
<223> OTHER INFORMATION: Xaa is absent, Tyr, His, Thr, Gly or Asp
<220> FEATURE:
```

-continued

```
<221> NAME/KEY: MISC_FEATURE
<222> LOCATION: (30)..(30)
<223> OTHER INFORMATION: Xaa is absent, Thr, Asn, Asp, Gln, His, Lys,
      Gly, Arg, Pro, Ser or Glu
<220> FEATURE:
<221> NAME/KEY: MISC_FEATURE
<222> LOCATION: (31)..(31)
<223> OTHER INFORMATION: Xaa is absent, Pro, His, Gly or Asp
<220> FEATURE:
<221> NAME/KEY: MISC_FEATURE
<222> LOCATION: (32)..(32)
<223> OTHER INFORMATION: Xaa is absent, Lys or Gln
<220> FEATURE:
<221> NAME/KEY: MISC_FEATURE
<222> LOCATION: (33)..(33)
<223> OTHER INFORMATION: Xaa is absent or Thr
<220> FEATURE:
<221> NAME/KEY: MISC_FEATURE
<222> LOCATION: (34)..(34)
<223> OTHER INFORMATION: Xaa is absent or Leu
<220> FEATURE:
<221> NAME/KEY: MISC_FEATURE
<222> LOCATION: (35)..(35)
<223> OTHER INFORMATION: Xaa is absent or Glu

<400> SEQUENCE: 2

Xaa Xaa Xaa Xaa Xaa Xaa Xaa His Leu Cys Gly Ser Xaa Leu Val Glu
1               5                   10                  15

Ala Leu Xaa Leu Val Cys Gly Glu Arg Gly Xaa Xaa Xaa Xaa Xaa Xaa
            20                  25                  30

Xaa Xaa Xaa
        35

<210> SEQ ID NO 3
<211> LENGTH: 21
<212> TYPE: PRT
<213> ORGANISM: Artificial
<220> FEATURE:
<223> OTHER INFORMATION: Modified insulin A chain
<220> FEATURE:
<221> NAME/KEY: MISC_FEATURE
<222> LOCATION: (8)..(8)
<223> OTHER INFORMATION: Xaa is Thr or His
<220> FEATURE:
<221> NAME/KEY: MISC_FEATURE
<222> LOCATION: (12)..(12)
<223> OTHER INFORMATION: Xaa is Ser, Asp or Glu
<220> FEATURE:
<221> NAME/KEY: MISC_FEATURE
<222> LOCATION: (13)..(13)
<223> OTHER INFORMATION: Xaa is Leu, Thr, Asn, Asp, Gln, His, Lys, Gly,
      Arg, Pro, Ser or Glu
<220> FEATURE:
<221> NAME/KEY: MISC_FEATURE
<222> LOCATION: (14)..(14)
<223> OTHER INFORMATION: Xaa is Thr, Asn, Asp, Gln, His, Lys, Gly, Arg,
      Pro, Ser or Glu
<220> FEATURE:
<221> NAME/KEY: MISC_FEATURE
<222> LOCATION: (15)..(15)
<223> OTHER INFORMATION: Xaa is Gln, Asp or Glu
<220> FEATURE:
<221> NAME/KEY: MISC_FEATURE
<222> LOCATION: (18)..(18)
<223> OTHER INFORMATION: Xaa is Asn, Lys or Gln
<220> FEATURE:
<221> NAME/KEY: MISC_FEATURE
<222> LOCATION: (21)..(21)
<223> OTHER INFORMATION: Xaa is Asn or Gln

<400> SEQUENCE: 3

Gly Ile Val Glu Gln Cys Cys Xaa Ser Ile Cys Xaa Xaa Xaa Xaa Leu
1               5                   10                  15
```

Glu Xaa Tyr Cys Xaa
            20

<210> SEQ ID NO 4
<211> LENGTH: 30
<212> TYPE: PRT
<213> ORGANISM: Artificial
<220> FEATURE:
<223> OTHER INFORMATION: Modified insulin B chain
<220> FEATURE:
<221> NAME/KEY: MISC_FEATURE
<222> LOCATION: (1)..(1)
<223> OTHER INFORMATION: Xaa is Phe or Glu
<220> FEATURE:
<221> NAME/KEY: MISC_FEATURE
<222> LOCATION: (3)..(3)
<223> OTHER INFORMATION: Xaa is Asn or Gln
<220> FEATURE:
<221> NAME/KEY: MISC_FEATURE
<222> LOCATION: (4)..(4)
<223> OTHER INFORMATION: Xaa is Gln or Glu
<220> FEATURE:
<221> NAME/KEY: MISC_FEATURE
<222> LOCATION: (10)..(10)
<223> OTHER INFORMATION: Xaa is His, Asp, Pro or Glu
<220> FEATURE:
<221> NAME/KEY: MISC_FEATURE
<222> LOCATION: (16)..(16)
<223> OTHER INFORMATION: Xaa is Tyr, Asp, Gln, His, Arg or Glu
<220> FEATURE:
<221> NAME/KEY: MISC_FEATURE
<222> LOCATION: (24)..(24)
<223> OTHER INFORMATION: Xaa is Phe or His
<220> FEATURE:
<221> NAME/KEY: MISC_FEATURE
<222> LOCATION: (26)..(26)
<223> OTHER INFORMATION: Xaa is absent, Tyr, His, Thr, Gly or Asp
<220> FEATURE:
<221> NAME/KEY: MISC_FEATURE
<222> LOCATION: (27)..(27)
<223> OTHER INFORMATION: Xaa is absent, Thr, Asn, Asp, Gln, His, Lys,
      Gly, Arg, Pro, Ser or Glu
<220> FEATURE:
<221> NAME/KEY: MISC_FEATURE
<222> LOCATION: (28)..(28)
<223> OTHER INFORMATION: Xaa is absent, Pro, His, Gly or Asp
<220> FEATURE:
<221> NAME/KEY: MISC_FEATURE
<222> LOCATION: (29)..(29)
<223> OTHER INFORMATION: Xaa is absent, Lys or Gln
<220> FEATURE:
<221> NAME/KEY: MISC_FEATURE
<222> LOCATION: (30)..(30)
<223> OTHER INFORMATION: Xaa is absent or Thr

<400> SEQUENCE: 4

Xaa Val Xaa Xaa His Leu Cys Gly Ser Xaa Leu Val Glu Ala Leu Xaa
1               5                   10                  15

Leu Val Cys Gly Glu Arg Gly Xaa His Xaa Xaa Xaa Xaa Xaa
            20                  25                  30

<210> SEQ ID NO 5
<211> LENGTH: 21
<212> TYPE: PRT
<213> ORGANISM: Artificial
<220> FEATURE:
<223> OTHER INFORMATION: The A chain of examples 1-4 & 12-19.

<400> SEQUENCE: 5

Gly Ile Val Glu Gln Cys Cys Thr Ser Ile Cys Ser Leu Glu Gln Leu
1               5                   10                  15

Glu Asn Tyr Cys Asn
            20

```
<210> SEQ ID NO 6
<211> LENGTH: 28
<212> TYPE: PRT
<213> ORGANISM: Artificial
<220> FEATURE:
<223> OTHER INFORMATION: The B chain specified in examples 1-5 & 12-19.

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe His Tyr Thr Pro
            20                  25

<210> SEQ ID NO 7
<211> LENGTH: 21
<212> TYPE: PRT
<213> ORGANISM: Artificial
<220> FEATURE:
<223> OTHER INFORMATION: The A chain of example 5.

<400> SEQUENCE: 7

Gly Ile Val Glu Gln Cys Cys Thr Ser Ile Cys Ser Leu Tyr Gln Leu
1               5                   10                  15

Glu Asn Tyr Cys Asn
            20
```